US011771332B2

(12) United States Patent
Min et al.

(10) Patent No.: US 11,771,332 B2
(45) Date of Patent: Oct. 3, 2023

(54) METHOD FOR DETECTING WEAR USING PLURALITY OF SENSORS AND ELECTRONIC DEVICE IMPLEMENTING SAME

(71) Applicant: Samsung Electronics Co., Ltd., Gyeonggi-do (KR)

(72) Inventors: Eungi Min, Gyeonggi-do (KR); Jeahyuck Lee, Gyeonggi-do (KR); Yong Jin Lee, Seoul (KR); Seung-Eun Lee, Seoul (KR)

(73) Assignee: Samsung Electronics Co., Ltd

( * ) Notice: Subject to any disclaimer, the term of this patent is extended or adjusted under 35 U.S.C. 154(b) by 631 days.

(21) Appl. No.: 16/767,949

(22) PCT Filed: Oct. 22, 2018

(86) PCT No.: PCT/KR2018/012490
§ 371 (c)(1),
(2) Date: May 28, 2020

(87) PCT Pub. No.: WO2019/107741
PCT Pub. Date: Jun. 6, 2019

(65) Prior Publication Data
US 2020/0367827 A1 Nov. 26, 2020

(30) Foreign Application Priority Data

Dec. 1, 2017 (KR) .................. 10-2017-0163976

(51) Int. Cl.
*A61B 5/024* (2006.01)
*A61B 5/00* (2006.01)
(Continued)

(52) U.S. Cl.
CPC ...... *A61B 5/02416* (2013.01); *A61B 5/02438* (2013.01); *A61B 5/681* (2013.01);
(Continued)

(58) Field of Classification Search
CPC . A61B 5/02416; A61B 5/02438; A61B 5/681; A61B 5/6843; A61B 5/7285;
(Continued)

(56) References Cited

U.S. PATENT DOCUMENTS

2015/0157269 A1* 6/2015 Lisogurski ........... A61B 5/0295
600/301
2015/0173631 A1* 6/2015 Richards .............. A61B 5/7282
600/479
(Continued)

FOREIGN PATENT DOCUMENTS

KR   1020120103129    9/2012
KR   10-1571262       11/2015
(Continued)

OTHER PUBLICATIONS

Korean Office Action dated Aug. 26, 2022 issued in counterpart application No. 10-2017-0163976, 9 pages.
(Continued)

*Primary Examiner* — Thanh Luu
(74) *Attorney, Agent, or Firm* — The Farrell Law Firm, P.C.

(57) ABSTRACT

Various embodiments provide an electronic device and a method, the device comprising: a capacitive sensor, a heart rate sensor including at least one light-emitting unit, a first light receiving unit, and a second light receiving unit; and a processor, wherein the processor is configured to: measure capacitance for a user wearing the electronic device by using the capacitive sensor; emit light by using the light-emitting unit according to the capacitance; measure a first amount of light which is said light reflected by the user's body tissue through the first light receiving unit, and a second amount of light which is said light reflected by the body tissue through the second light receiving unit; determine that the electronic device is worn by the user when at least one amount of light
(Continued)

of the first amount of light and the second amount of light satisfies an amount of light in a specified range; and determine that the electronic device is detached from the user when the first amount of light and the second amount of light do not satisfy the amount of light in the specified range. Also, other embodiments are possible.

13 Claims, 16 Drawing Sheets

(51) Int. Cl.
  *G01D 5/24* (2006.01)
  *G01J 1/44* (2006.01)
  *G06F 3/03* (2006.01)
  *A61B 5/053* (2021.01)
(52) U.S. Cl.
  CPC .......... *A61B 5/6843* (2013.01); *A61B 5/7285* (2013.01); *G01D 5/24* (2013.01); *G01J 1/44* (2013.01); *G06F 3/0304* (2013.01); *A61B 5/053* (2013.01)
(58) Field of Classification Search
  CPC ........ A61B 5/053; A61B 5/6844; G01D 5/24; G01J 1/44; G06F 3/0304; G06F 1/16; G06F 3/01; G06F 3/033; G06F 21/32; G06F 3/011; G06F 1/163; G06F 2203/011
  See application file for complete search history.

(56) References Cited

U.S. PATENT DOCUMENTS

| | | | |
|---|---|---|---|
| 2015/0185918 A1* | 7/2015 | Backman | G06F 3/04166 345/174 |
| 2015/0358088 A1 | 12/2015 | Eim et al. | |
| 2016/0026212 A1* | 1/2016 | Lee | G06F 1/3231 361/679.03 |
| 2016/0154952 A1* | 6/2016 | Venkatraman | G06Q 20/40145 726/19 |
| 2016/0199002 A1 | 7/2016 | Lee et al. | |
| 2018/0098708 A1 | 4/2018 | Lee | |

FOREIGN PATENT DOCUMENTS

| | | |
|---|---|---|
| KR | 1020150140150 | 12/2015 |
| KR | 1020160009741 | 1/2016 |
| KR | 1020160122595 | 10/2016 |
| KR | 1020170019127 | 2/2017 |

OTHER PUBLICATIONS

PCT/ISA/210 Search Report issued on PCT/KR2018/012490 pp. 5.
PCT/ISA/237 Written Opinion issued on PCT/KR2018/012490, pp. 6.
KR Notice of Patent Grant dated Feb. 25, 2023 issued in counterpart application No. 10-2017-0163976, 5 pages.

* cited by examiner (1410)

(1420)

(1430)

(1440)

though the wearable device is worn, the wearable device including one light-receiving unit may be recognized as a non-wear state, because the capacitive sensor is irregularly detached from the user's body in an unstable wear situation (e.g., a lot of movement, or a loosely joint state).

METHOD FOR DETECTING WEAR USING PLURALITY OF SENSORS AND ELECTRONIC DEVICE IMPLEMENTING SAME

PRIORITY

This application is a National Phase Entry of International Application No. PCT/KR2018/012490, which was filed on Oct. 22, 2018, and claims priority to Korean Patent Application No. 10-2017-0163976, filed in the Korean Intellectual Property Office on Dec. 1, 2017, the content of each of which is incorporated herein by reference.

TECHNICAL FIELD

Various embodiments relate to a method and apparatus for sensing wear by using a plurality of sensors.

BACKGROUND ART

A wearable device, a kind of an electronic device, can be worn on the user's body, measure a biometric signal of a user from one or more electrodes and sensors installed in the wearable device, and, by using the measured biometric signal, provide various biometric information of the user such as a heart rate, the number of walks, a sleeping state, stress information, body fat information, a calories consumption amount, etc. In recent years, by using user authentication for identity identification, the wearable device is providing various services of online payment, e-banking, car and permission area access, other device connection, etc.

The user authentication using the wearable device can use a scheme of utilizing an identity identification device installed in the wearable device or utilizing user authentication information of a mobile device interlocked. Also, the wearable device can determine whether a user wears the wearable device, and provide a mutually different use environment (e.g., locking or unlocking) according to a wear state or a non-wear state. In an example, the wearable device can determine wear or non-wear by using a capacitive sensing technology. The capacitive sensing technology is a technology for sensing proximity, displacement, humidity, flux, etc. by using an amount of variation of capacitance, and can be used for a touch sensor of an electronic device such as a portable phone and a tablet personal computer (PC) or the sensing of wear of the wearable device.

DISCLOSURE OF INVENTION

Technical Problem

By using a capacitive sensor, a wearable device can determine whether the wearable device is worn by a user. However, the capacitive sensor, a sensor for sensing a very small variation of capacitance, may be efficient for sensing whether the wearable device is worn continuously in a stable situation (e.g., less movement, or a tightly joint state). However, even though the wearable device is worn, the wearable device including one light-receiving unit may be recognized as a non-wear state, because the capacitive sensor is irregularly detached from the user's body in an unstable wear situation (e.g., a lot of movement, or a loosely joint state).

Various embodiments may present a method and apparatus for accurately judging whether a wearable device is worn by a user, to smoothly present various biometric information and various services other than the biometric information presenting.

Various embodiments may present a method and apparatus for accurately judging whether a wearable device is worn by a user, by using a plurality of sensors.

Solution to Problem

An electronic device of various embodiments may include a capacitive sensor; a heart rate sensor including at least one light-emitting unit, a first light-receiving unit, and a second light-receiving unit; and a processor. The processor may be configured to measure capacitance for a user wearing the electronic device by using the capacitive sensor, emit light by using the light-emitting unit according to the capacitance, measure a first amount of light into which the light is reflected by the user's body tissue through the first light-receiving unit, and a second amount of light into which the light is reflected by the body tissue through the second light-receiving unit, determine that the electronic device is worn by the user in response to at least one amount of light among the first amount of light and the second amount of light satisfying a specified amount of light, and determine that the electronic device is detached from the user in response to the first amount of light and the second light not satisfying the specified amount of light.

An electronic device of various embodiments may include a capacitive sensor; a heart rate sensor including at least one light-emitting unit and at least one light-receiving unit; and a processor. The processor may be configured to measure capacitance for a user wearing the electronic device, by using the capacitive sensor, emit light by using the light-emitting unit according to the capacitance, measure an amount of light into which the light is reflected by the user's body tissue through the at least one light-receiving unit, and in response to the amount of light satisfying a first specified condition, determine that the electronic device is worn by the user, and in response to the amount of light satisfying a second specified condition, emit light by using the light-emitting unit, sense light into which the emitted light is reflected according to a blood flow rate of the user's blood vessel, sense a biometric signal for the user by using the reflected light, and determine that the electronic device is worn by the user, at least based on the biometric signal.

An electronic device of various embodiments may include a capacitive sensor; a heart rate sensor including at least one light-emitting unit and at least one light-receiving unit; and a processor. The processor may be configured to measure capacitance for a user wearing the electronic device, by using the capacitive sensor, measure an amount of light through the at least one light-receiving unit according to the capacitance, and in response to the amount of light satisfying a first specified condition, determine that the electronic device is worn by the user, and in response to the amount of light satisfying a second specified condition, emit light of a specified brightness by using the light-emitting unit, sense light into which the emitted light is reflected by the user through the at least one light-emitting unit, sense a biometric signal for the user by using the reflected light, and determine that the electronic device is worn by the user, at least based on the biometric signal.

Advantageous Effects of Invention

According to various embodiments, the present disclosure may more accurately determine a wear/non-wear state of a user based on a signal obtained in each light-receiving unit, by turning On/Off a switch coupled to a plurality of light-receiving units of an optical sensor installed in a wearable device in response to a capacitance value measured by a capacitive sensor installed in a wearable device not exceeding a threshold value.

According to various embodiments, the present disclosure may complement a disadvantage of a wear sensing technique of a capacitive sensing scheme of, in response to a wearable device being somewhat spaced apart from the user's body, failing to recognize a wear state although a user is wearing the wearable device.

According to various embodiments, the present disclosure may sense whether the same person continuously wears a wearable device based on a wear sensing solution of a capacitive sensing scheme and an optical scheme.

According to various embodiments, the present disclosure may more accurately determine a wear/non-wear state of a user, by judging whether the user wears the wearable device by using a DC signal obtained from a light-receiving unit of an optical sensor installed in the wearable device and additionally judging whether the user wears the wearable device by using an AC signal obtained from the light-receiving unit.

BEST MODE FOR CARRYING OUT THE INVENTION

Figure 1:
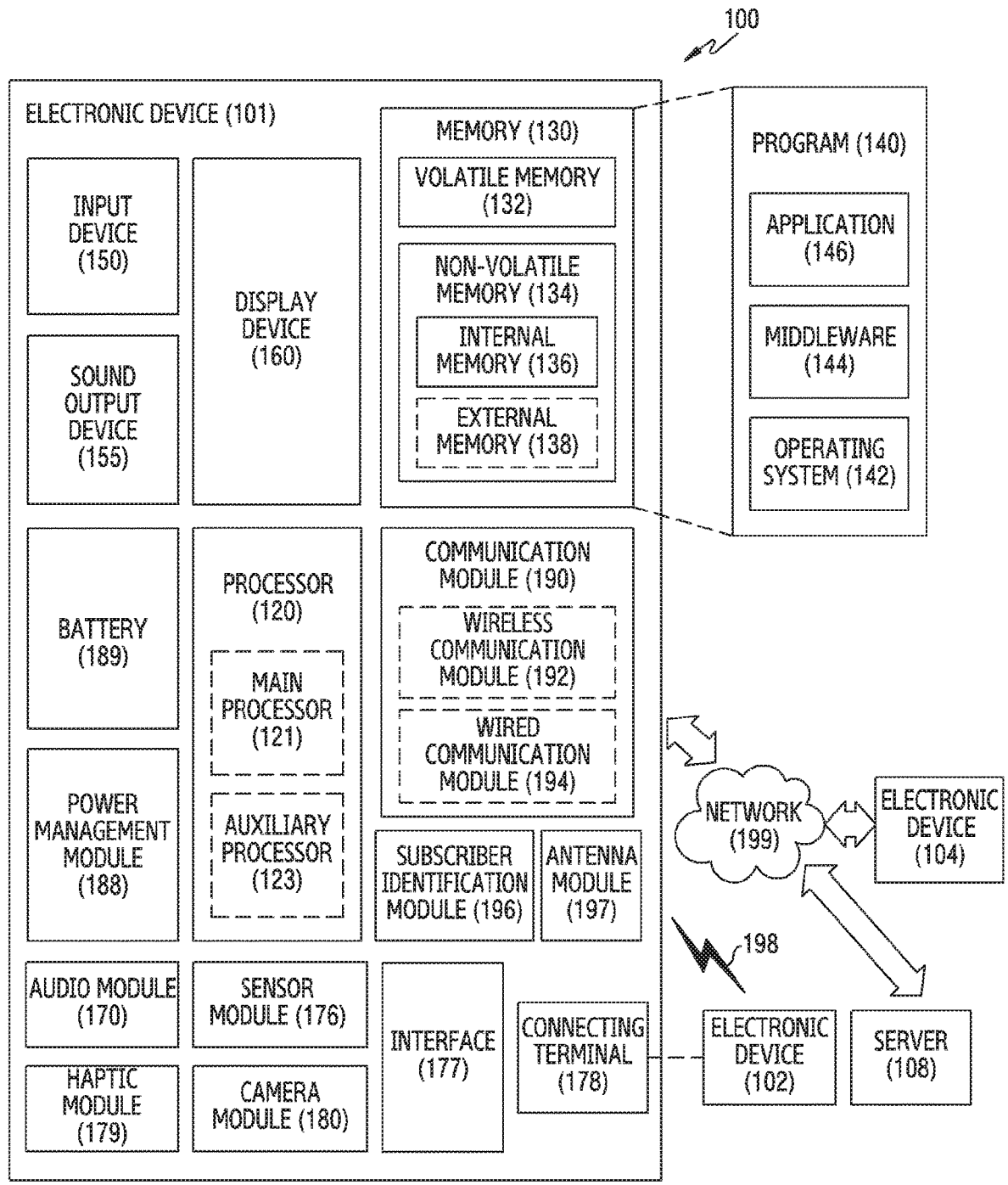
FIG. 1 is a block diagram of an electronic device within a network environment according to various embodiments.

Various embodiments of the present document are mentioned below with reference to the accompanying drawings. An embodiment and terms used therein do not intend to limit the technologies mentioned in the present document to a specific embodiment form, and should be understood to include various modifications, equivalents, and/or alternatives of the corresponding embodiment. With regard to a description of the drawings, like reference numerals may be used to refer like components. And, an embodiment disclosed in the present disclosure has been suggested for explanation and understanding of the technology content disclosed, and does not limit the scope of the technology mentioned in the present disclosure. Accordingly, the scope of the present disclosure should be interpreted as including all changes or various other embodiments that are based on the technological spirit of the present disclosure.

FIG. 1 is a block diagram illustrating an electronic device 101 in a network environment 100 according to various embodiments.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse or a keyboard.

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or a pressure sensor (or a force sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or an external electronic device (e.g., an electronic device 102 (e.g., a speaker or a headphone)) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, a barometer sensor, a magnetic sensor, an acceleration sensor, a grip sensor, a proximity sensor, a color sensor (e.g., RGB (red, green, blue) sensor), an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wired) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other.

The wireless communication module 192 may identify and authenticate the electronic device 101 in a communication network using subscriber information stored in the subscriber identification module 196.

The antenna module 197 may include at least one antenna for transmitting or receiving a signal or power to or from the outside (e.g., the external electronic device).

According to an embodiment, the communication module 190 (e.g., the wireless communication module 192) may transmit or receive the signal to or from the external electronic device through at least one antenna appropriate for a communication scheme used in the communication network.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101.

According to an embodiment, all or some of operations to be executed at the electronic device 101 may be executed at one or more of the external electronic devices 102 or 104. For example, if the electronic device 101 should perform a function or a service automatically, or in response to a request from a user or another device, the electronic device 101, instead of, or in addition to, executing the function or the service, may request the one or more external electronic devices 102 or 104 to perform at least part of the function or the service. The one or more external electronic devices 102 or 104 receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
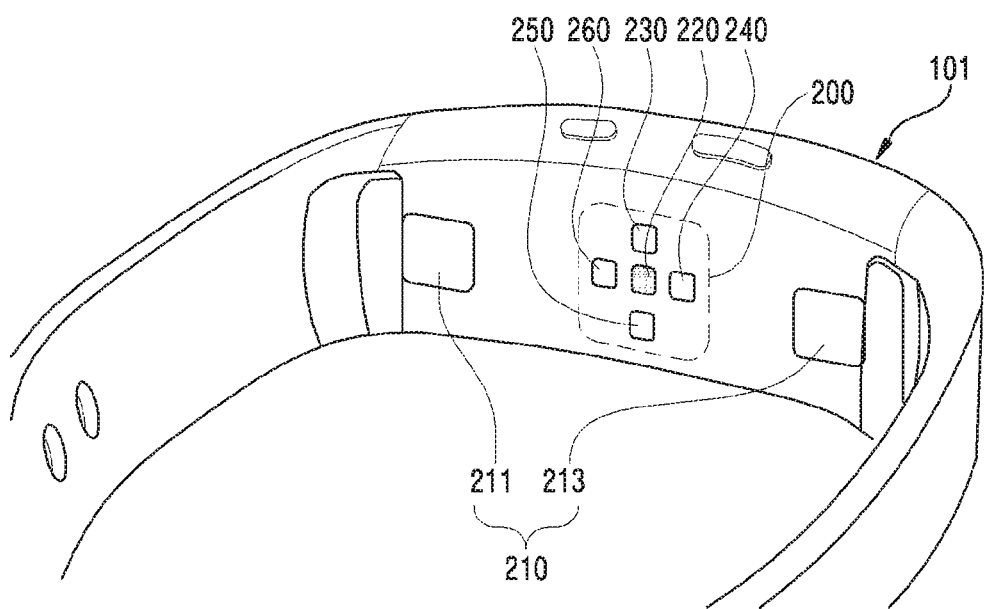
FIG. 2 is a diagram illustrating an external shape of an electronic device according to various embodiments.

FIG. 2 is a diagram illustrating an external shape of an electronic device according to various embodiments.

Referring to FIG. 2, the electronic device 101 may be a wrist-on type wearable device (e.g., a watch) which may be worn on the user's body (e.g., the wrist). According to various embodiments, the electronic device 101 may include a housing (or a main body) and a coupling part (e.g., a strap) installed in the housing. A front surface of the housing may include a display (e.g., the display device 160). According to cases, the display may include a touch screen, and receive a touch input. A rear surface of the housing may include a capacitive sensor 210 and an optical sensor which includes a light-emitting unit 220 and one or more light-receiving units 230 to 260.

The capacitive sensor 210 may be comprised of at least two electrodes. For example, the capacitive sensor 210 may include a first electrode 211 and a second electrode 213. The capacitive sensor 210 may get in direct contact with the user's body (e.g., the skin), and may determine whether the electronic device 101 has been worn (e.g., wrist on) or has not been worn (e.g., wrist off) by a user according to skin contact or non-contact. A capacitive sensor measurement value (Csensor) in response to a conductive material (e.g., the user's body) not approaching the first electrode 211 and the second electrode 213 for measuring a variation of capacitance may be the same as a capacitance value (Cenv) by the peripheral environment. In response to the conductive material such as the finger or the wrist approaching or getting in contact with the first electrode 211 and the second electrode 213, a measurement value of the capacitive sensor 210 may be increased by a variation of an electric field. For example, in response to the measurement value of the capacitive sensor 210 being out of a first range (or a threshold value, or a specified value, or a specified range), the processor (e.g., the processor 120) may determine that the electronic device 101 is worn by the user. In response to the measurement value being within the first range, the processor may determine that the electronic device 101 is detached from (or is not worn by) the user. However, there may be an error in judging wear or detachment (or non-wear) by using only the capacitive sensor 210, according to a wear habit, exercise or non-exercise, or behavior pattern of the user (e.g., a person loosely wearing, a person tightly wearing, etc.) who wears the electronic device 101. The arrangement of the first electrode 211 or the second electrode 213 is not limited to the illustrated example.

The optical sensor may include the light-emitting unit 220 and one or more light-receiving units 230 to 260. The optical sensor may be one outputting light and measuring an amount of light reflected by the outputted light, to sense a biometric signal of a user. For example, the optical sensor may be a photoplethysmography (PPG) sensor, which is a kind of a heart rate sensor. Below, the optical sensor has been described as the heart rate sensor for description convenience's sake, but the optical sensor is not limited to the heart rate sensor by the description. The PPG sensor may be one using a principle in which a degree of absorption and reflection of light is varied according to a variation of a thickness of the blood vessel dependent on a heartbeat. According to various embodiments, the PPG sensor may be comprised of the light-emitting unit 220 emitting light and at least one light-receiving unit 230 to 260 sensing light which is irradiated from the light-emitting unit 220 to the user's body and is reflected. A magnitude of a value measured in the light-receiving unit is varied according to a blood flow rate varied by a heartbeat, and a varied cycle may be measured to acquire a photoplethysmography (PPG) signal. In accordance with an embodiment, light emitted through the PPG sensor or light sensed may include a variety of light (e.g., infrared ray, or green light) for sensing a biometric signal of a user.

According to various embodiments, the light-emitting unit 220 may use a green LED resistant to noise. In the drawings, it is illustrated that one light-emitting unit 220 is constructed but, in response to the light-emitting unit 220 being constructed to have two mutually different wavelengths, a heart rate and concurrently an oxygen saturation may be measured. For example, in response to red and IR LEDs being added, a stress, an oxygen saturation, or a blood pressure, etc. may be measured. Or, in response to a blue LED being added, a blood sugar may be measured. At least one of various LEDs may exist according to biometric information intended to be measured. The plurality of light-receiving units 230 to 260 may include the first light-receiving unit 230, the second light-receiving unit 240, the third light-receiving unit 250 and the fourth light-receiving unit 260. Light emitted by the light-emitting unit 220 may be absorbed by the user's body tissue, and partial light may be reflected by the user's skin or a blood flow of the blood vessel, and be received by the plurality of light-receiving units 230 to 260. In the drawings, it is illustrated that four light-receiving units are constructed, but the light-receiving unit may be one or more.

Figure 3:
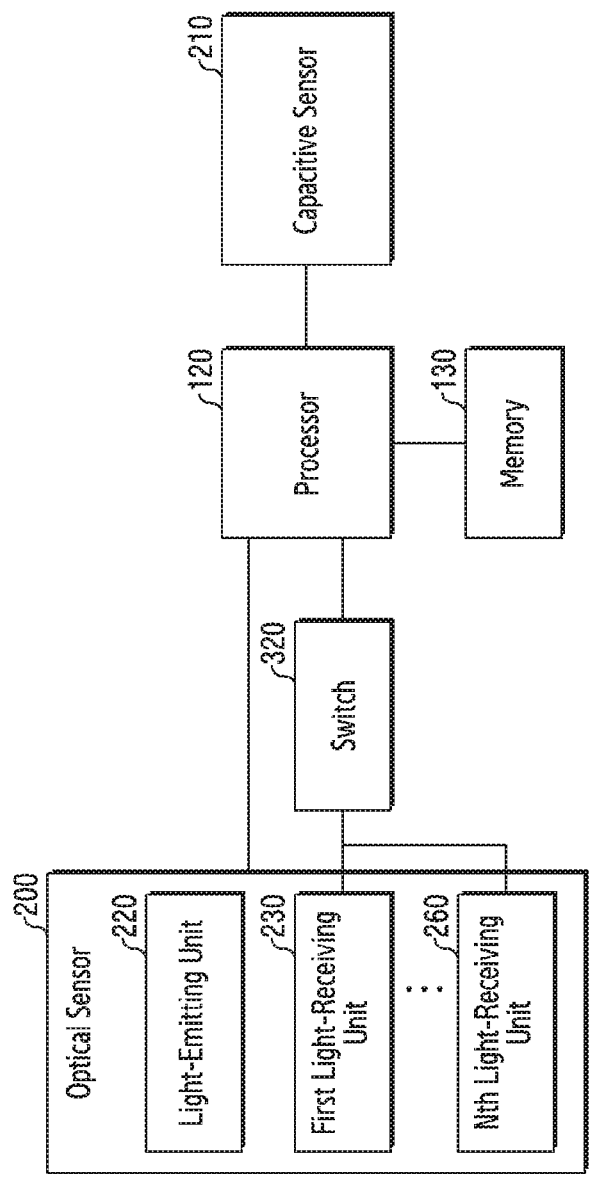
FIG. 3 is a block diagram illustrating a construction of an electronic device according to various embodiments.

FIG. 3 is a block diagram illustrating a construction of an electronic device according to various embodiments.

Referring to FIG. 3, the electronic device 101 may include the processor 120, the memory 130, the capacitive sensor 210, the optical sensor 200, and a switch 320.

The processor 120 may control functions of the capacitive sensor 210 and the optical sensor 200, and determine the wear or detachment of the electronic device 101 through an algorithm raw data measured from the capacitive sensor 210 and the optical sensor 200. For example, the processor 120 may primarily determine the wear or non-wear of the electronic device 101 based on a capacitance value received (or measured) from the capacitive sensor 210. In response to the measured capacitance value being out of a first range, the processor 120 may determine that the electronic device 101 is worn by a user. Or, in response to the measured capacitance value being within the first range, the processor 120 may determine that the electronic device 101 is detached from the user. In response to it being primarily determined that the electronic device 101 is detached, the processor 120 may control the switch 320 coupled to the optical sensor 200. According to various embodiments, the switch 320 may be comprised of a plurality of switches to selectively couple the plurality of light-receiving units 230 to 260 and the processor.

In a general situation (e.g., in response to it being determined that the electronic device 101 is worn), the processor 120 may measure a biometric signal by using output values received (or measured) from the plurality of light-receiving units 230 to 260. For example, in the general situation, the processor 120 may turn On all the switch 320 and receive output values from the plurality of light-receiving units 230 to 260. For the sake of biometric signal measurement, the processor 120 may need an output value (e.g., an AC output value) received during a predetermined time (e.g., 5 seconds, 10 seconds, etc.). The processor 120 may store the measured biometric signal in the memory 130. But, in a situation where it is determined by the capacitive sensor 210 that the electronic device 101 is detached, the processor 120 may control the switch 320 in order to receive only an output of any one light-receiving unit among the plurality of light-receiving units 230 to 260 (e.g., any one of the first light-receiving unit 230, the second light-receiving unit 240, the third light-receiving unit 250, and the fourth light-receiving unit 260).

In various embodiments, turning On the switch 320 may include closing the switch 320. The switch 320 is closed, whereby an electric current may flow in a region including the switch 320. Turning Off the switch 320 may include opening the switch 320. The switch 320 is opened, whereby an electric current may not flow in the region including the switch 320.

For example, in a situation where it is determined that the electronic device 101 is detached, the processor 120 may turn On or Off the switch 320 and receive only a value outputted from any one light-receiving unit. The processor 120 may turn On a switch coupled to the first light-receiving unit 230 and turn Off a switch coupled to the Nth light-receiving unit 260, and determine whether the electronic device 101 is worn based on an output value (e.g., a direct current output value) received from the first light-receiving unit 230. In response to the output value received from the first light-receiving unit 230 being within a second range (or a threshold value, or a specified value, or a specified range), the processor 120 may determine that the electronic device 101 is worn, and turn On all the switch 320. But, in response to the output value received from the first light-receiving unit 230 being out of the second range, the processor 120 may determine that the electronic device 101 is detached. In this case, the processor 120 may turn Off the switch coupled to the first light-receiving unit 230 and turn On the switch coupled to the Nth light-receiving unit 260, and determine whether the electronic device 101 is worn based on an output value (e.g., a direct current output value) received from the Nth light-receiving unit 260. In response to the output value received from the Nth light-receiving unit 260 being within the second range, the processor 120 may determine that the electronic device 101 is worn, and turn On all the switch 320. But, in response to the output value received from the Nth light-receiving unit 260 being out of the second range, the processor 120 may determine that the electronic device 101 is detached. In response to each output value (e.g., direct current output value) outputted from each light-receiving unit being all obtained out of the second range, the processor 120 may determine that the electronic device 101 is detached. For example, the direct current output value may be obtained low at a wear state, and be obtained high at a detachment state. That is because in the detachment state, light is received by the light-receiving unit even from an external light source (e.g., sunlight and fluorescent lamp light) besides light emitted from the light-emitting unit 220, so much light may be obtained in the light-receiving unit.

The processor 120 of various embodiments may control an intensity of light of the light-emitting unit 220 or an output cycle of light, etc. The processor 120 may obtain a direct current output value (e.g., DC value) or an alternating current output value (e.g., AC value) based on an amount of light received by a plurality of light-receiving units (e.g., the first light-receiving unit 230 to the Nth light-receiving unit 260). The direct current output value may be an amount of light into which light emitted by the light-emitting unit 220 is reflected by the user's body tissue. The direct current output value may be acquired within a relatively short time, because the direct current output value is measured using a value which is obtained during a time of a few ms or less. The alternating current output value may be an amount of light into which light emitted by the light-emitting unit 220 is reflected according to a blood flow rate of the user's blood vessel. The alternating current output value is obtained using an output value which is acquired during a predetermined time (e.g., 5 seconds, 10 seconds, etc.) and thus, an acquisition time may be longer than that of the direct current output value. By using the direct current output value, the processor 120 may primarily obtain the wear or non-wear of the electronic device 101 and, by using the alternating current output value, the processor 120 may secondarily obtain the wear or non-wear of the electronic device 101.

In response to each output value (e.g., a direct current electric current value) outputted from each light-receiving unit being all obtained out of the second range, the processor 120 of various embodiments may adjust an intensity of light of the light-emitting unit 220. The processor 120 may increase the intensity of light of the light-emitting unit 220, and obtain the wear or non-wear of the electronic device 101 by using the alternating current output value. By using an output value received during a predetermined time, the processor 120 may acquire a biometric signal (e.g., a plethysmogram signal). In response to the biometric signal being acquired, the processor 120 may determine that the electronic device 101 is worn. But, in response to the biometric signal not being acquired, the processor 120 may determine that the electronic device 101 is detached.

The processor 120 of various embodiments may perform user authentication based on the wear or non-wear of the electronic device 101, or control (e.g., lock or unlock) the electronic device 101 based on the user authentication.

The memory 130 may store a lookup table for per-situation judgment dependent on a combination of output vales of the capacitive sensor 210 and the optical sensor 200. Below, Table 1 shows a lookup table.

TABLE 1

| Situation | Capacitive sensor output | Optical sensor output | Electronic device state |
|---|---|---|---|
| 1 | 1 | 1 | Wear state |
| 2 | 0 | 1 | Wear state |
| 3 | 0 | Output value 1 of at least one of plurality of light-receiving units | Wear state |
| 4 | 0 | Output value 0 of each of plurality of light-receiving units | Wear state or detachment state |
| 5 | 1 | 0 | Wear state |

The lookup table may include an output value of the optical sensor 200 (e.g., true (1) in response to being within the second range, and false (0) in response to being out of the second range) according to an output value of the capacitive sensor 210 (e.g., true (1) in response to being out of the first range, and false (0) in response to being within the first range). The output value of the optical sensor 200 may include an output value of at least one of the plurality of light-receiving units included in the optical sensor 200. For example, situations 1 and 5 may be states in which the capacitive sensor 210 installed in a rear surface of the electronic device 101 is in contact with the user's body. For example, situations 2 to 4 may be states for accurately sensing whether the electronic device 101 is worn on the user's body. That is, the situations 2 and 3 may be states in which it is determined to be a non-wear state by the capacitive sensor 210, but all output values of the plurality of light-receiving units 230 to 260 are within the second range, or an output value of at least one light-receiving unit is within the second range. That is, a situation may occur in which while a user enjoys a light exercise or a daily life, a wearable device is slightly spaced apart from the skin. Even in this case, the processor 120 may maintain a state of the electronic device 101 as a wear state. The processor 120 may maintain user authentication based on maintaining the wear state. The situation 4 may be a state in which it is determined to be a detachment state (or non-wear state) by the capacitive sensor 210, and all the output values of the plurality of light-receiving units 230 to 260 are out of the second range. By increasing an electric current of the light-emitting unit 220, the processor 120 may determine whether it is in a detachment state. By identifying an alternating current output value related to the increase, the processor 120 may determine whether it is in the detachment state. In some embodiments, in response to the alternating current output value being obtained, the processor 120 may determine the state of the electronic device 101 as the wear state. In other some embodiments, in response to the alternating current output value not being obtained, the processor 120 may determine the state of the electronic device 101 as the detachment state.

Figure 4A:
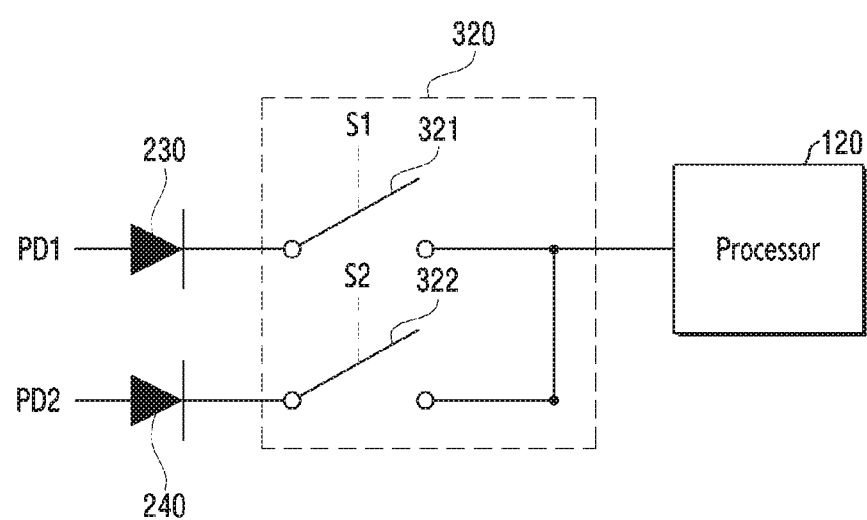
FIG. 4A to FIG. 4C are circuit diagrams illustrating a heart rate sensor and a switch of an electronic device according to various embodiments.
Figure 4B:
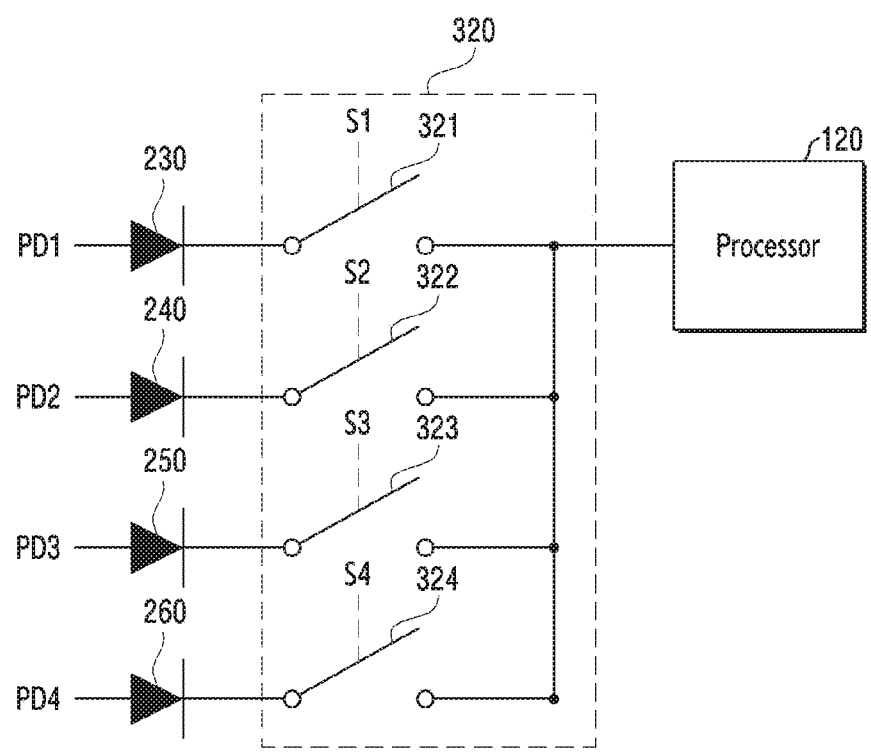
Figure 4C:
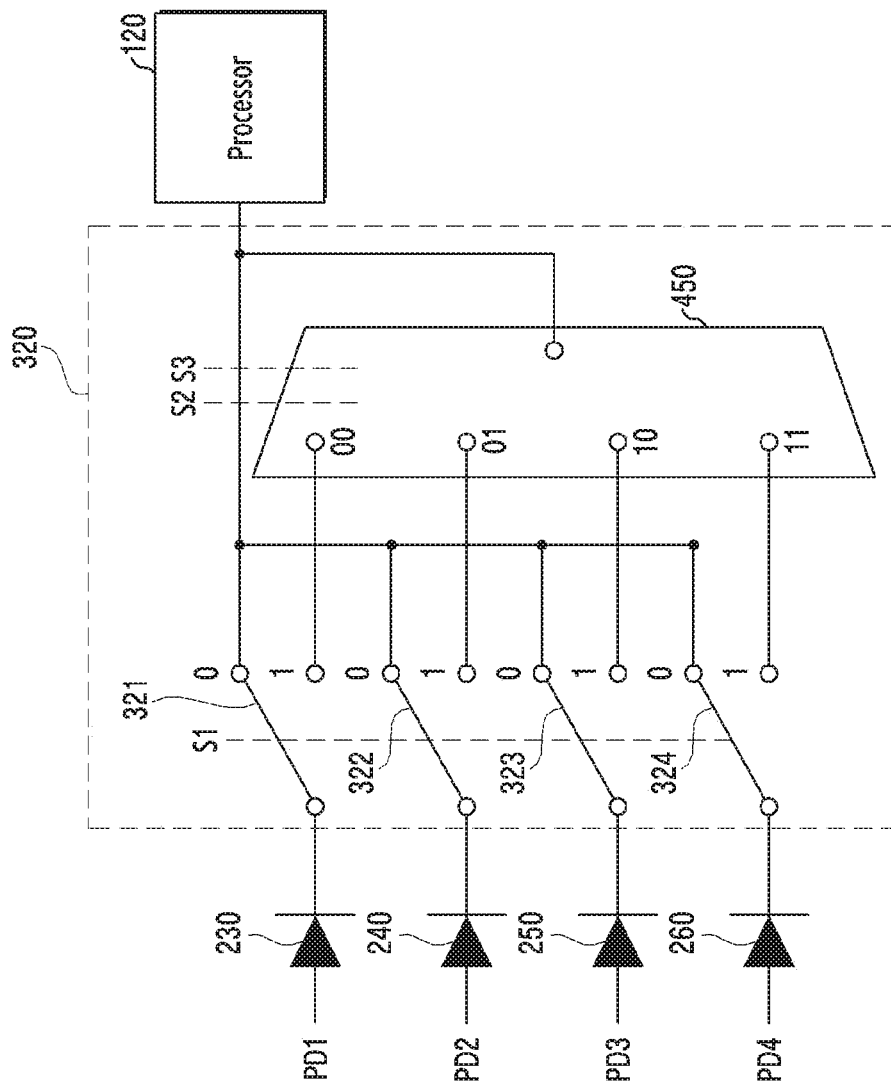

FIG. 4A to FIG. 4C are circuit diagrams illustrating a heart rate sensor and a switch of an electronic device according to various embodiments.

FIG. 4A illustrates a circuit diagram comprised of two light-receiving units 230 and 240 and two switches 321 and 322.

Referring to FIG. 4A, the first light-receiving units 230 (PD1) may be coupled with the first switch 321, and the second light-receiving units 240 (PD2) may be coupled with the second switch 322. The processor 120 may output a control signal (e.g., S1, S2) according to a situation. The first switch 321 and the second switch 322 may turn On or Off according to the control signal. Below, Table 2 shows an example of controlling the output of a light-receiving unit according to the control signal.

TABLE 2

|  | S1 | S2 | Output |
|---|---|---|---|
| Wear state | 1 | 1 | Output values of first and second light-receiving units |
| PD1 | 1 | 0 | Output value of first light-receiving unit |
| PD2 | 0 | 1 | Output value of second light-receiving unit |

Referring to Table 2, in response to the control signal (S1, S2) being '0', it may mean that the switch is in an open state (e.g., Off), and in response to the control signal being '1', it may mean that the switch is in a closed state (e.g., On). In a wear state (e.g., a normal mode), the first switch 321 and the second switch 322 all may be turned On. In a detachment (or non-wear) state, the first switch 321 may turn On and the second switch 322 turn Off (e.g., the output of the first light-receiving unit 230 is identified), or the first switch 321 may turn Off and the second switch 322 may turn On (e.g., the output of the second light-receiving unit 240 is identified). In response to an output value outputted from any one light-receiving unit among the first light-receiving unit 230 or the second light-receiving unit 240 satisfying a specified condition (e.g., within the second range), the processor 120 may determine as the wear state. In response to output values outputted from all of the first light-receiving unit 230 and the second light-receiving unit 240 not satisfying the specified condition (e.g., within the second range), the processor 120 may determine as the non-wear state.

FIG. 4B illustrates a circuit diagram comprised of four light-receiving units 230 to 260 and four switches 321 to 324.

Referring to FIG. 4B, the first light-receiving unit 230 (PD1) may be coupled with the first switch 321, and the second light-receiving unit 240 (PD2) may be coupled with the second switch 322, and the third light-receiving unit 250 (PD3) may be coupled with the third switch 323, and the fourth light-receiving unit 260 (PD4) may be coupled with the fourth switch 324. The processor 120 may output a control signal (e.g., S1, S2, S3, S4) according to a situation. The first switch 321 to the fourth switch 324 may be turned On or Off according to the control signal. Below, Table 3 shows an example of controlling the output of a light-receiving unit according to the control signal.

TABLE 3

|  | S1 | S2 | S3 | S4 | Output |
|---|---|---|---|---|---|
| Wear state | 1 | 1 | 1 | 1 | Output values of first to fourth light-receiving units |
| PD1 | 1 | 0 | 0 | 0 | Output value of first light-receiving unit |
| PD2 | 0 | 1 | 0 | 0 | Output value of second light-receiving unit |
| PD3 | 0 | 0 | 1 | 0 | Output value of third light-receiving unit |
| PD4 | 0 | 0 | 0 | 1 | Output value of fourth light-receiving unit |

Referring to Table 3, in response to the control signal (S1, S2, S3, S4) being '0', it may mean that the switch is in an open state (e.g., Off), and in response to the control signal being '1', it may mean that the switch is in a closed state (e.g., On). In a wear state (e.g., a normal mode), the first switch 321 to the fourth switch 324 all may be turned On. In a detachment (or non-wear) state, to identify the output of the first light-receiving unit 230, the processor 120 may turn On the first switch 321, and turn Off the second switch 322 to the fourth switch 324. In the detachment state, to identify the output of the second light-receiving unit 240, the processor 120 may turn On the second switch 322, and turn Off the first switch 321, the third switch 323, and the fourth switch 324. In the detachment state, to identify the output of the third light-receiving unit 250, the processor 120 may turn On the third switch 323, and turn Off the first switch 321, the second switch 322, and the fourth switch 324. In the detachment state, to identify the output of the fourth light-receiving unit 260, the processor 120 may turn On the fourth switch 324, and turn Off the first switch 321 to the third switch 323. In response to an output value outputted from any one light-receiving unit among the first light-receiving unit 230 or the fourth light-receiving unit 260 satisfying a specified condition (e.g., within the second range), the processor 120 may determine as a wear state. In response to output values outputted from all of the first light-receiving unit 230 to the fourth light-receiving unit 260 not satisfying the specified condition (e.g., within the second range), the processor 120 may determine as a non-wear state.

FIG. 4C illustrates a circuit diagram comprised of four light-receiving units 230 to 260, four switches 321 to 324, and a multiplexer 450.

Referring to FIG. 4C, the first light-receiving unit 230 (PD1) to the fourth light-receiving unit 260 (PD4) may be coupled with the first switch 321, and the multiplexer 450 may be coupled with the first switch 321. By outputting a control signal (e.g., S1, S2, S3) according to a situation and controlling the multiplexer 450, the processor 120 may acquire only an output value outputted from any one light-receiving unit among the first light-receiving unit 230 to the fourth light-receiving unit 260, and determine the wear or non-wear of the electronic device 101. Below, Table 4 shows an example of controlling the output of a light-receiving unit according to the control signal.

TABLE 4

|  | S1 | S2 | S3 | Output |
|---|---|---|---|---|
| Wear state | 0 | X | X | Output values of first to fourth light-receiving units |
| PD1 | 1 | 0 | 0 | Output value of first light-receiving unit |
| PD2 | 1 | 0 | 1 | Output value of second light-receiving unit |
| PD3 | 1 | 1 | 0 | Output value of third light-receiving unit |
| PD4 | 1 | 1 | 1 | Output value of fourth light-receiving unit |

Referring to Table 4, in response to the control signal (S1) being '0', it may mean that the switch is in a closed state (e.g., On), and in response to the control signal (S1) being '1', it may mean that the switch is in an open state (e.g., Off). In a wear state (e.g., a normal mode), the first switch 321 is all closed and thus output values of the first light-receiving unit 230 to the fourth light-receiving unit 260 may be inputted to the processor 120. In a detachment (or non-wear) state, the processor 120 may turn Off all the first switch 321. In response to the first switch 321 becoming in an Off state, the output of the first light-receiving unit 230 to the fourth light-receiving unit 260 may be inputted to the processor 120 via the multiplexer 450. In this case, the processor 120 may control the control signal (S1, S2), and output only a signal of any one of the first light-receiving unit 230 to the fourth light-receiving unit 260.

The electronic device 101 of various embodiments may include the capacitive sensor 210; the heart rate sensor 200 including the at least one light-emitting unit 220, the first light-receiving unit 230, and the second light-receiving unit 240; and the processor 120. The processor may be configured to measure capacitance for a user wearing the electronic device by using the capacitive sensor, emit light by using the light-emitting unit according to the capacitance, measure a first amount of light into which the light is reflected by the user's body tissue through the first light-receiving unit, and a second amount of light into which the light is reflected by the body tissue through the second light-receiving unit, determine that the electronic device is worn by the user in response to at least one amount of light among the first amount of light and the second amount of light satisfying an amount of light of a specified range, and determine that the electronic device is detached from the user in response to the first amount of light and the second amount of light not satisfying the amount of light of the specified range.

The processor may be configured to measure any one amount of light received from the first light-receiving unit or the second light-receiving unit in response to the measured capacitance being within a range.

The electronic device 101 may include the first switch 321 coupled with the first light-receiving unit, and the second switch 322 coupled with the second light-receiving unit 322. The processor may be configured to, in response to the measured capacitance being within a range, turn On the first switch and turn Off the second switch, and measure the first amount of light into which the light is reflected by the user's body tissue through the first light-receiving unit, or turn Off the first switch and turn On the second switch, and measure the second amount of light into which the light is reflected by the user's body tissue through the second light-receiving unit.

The processor may be configured to, in response to the first amount of light satisfying the specified amount of light, determine that the electronic device is worn by the user, and turn On the second switch.

The processor may be configured to, in response to the first amount of light not satisfying the specified amount of light, turn Off the first switch and turn On the second switch, and measure the second amount of light into which the light is reflected by the user's body tissue through the second light-receiving unit, and in response to the second amount of light satisfying the specified amount of light, determine that the electronic device is worn by the user, and turn On the first switch.

The processor may be configured to, in response to the first switch being turned On and the second switch being turned On and a combination of the first amount of light and the second amount of light being within a reference range, determine that the electronic device is worn by the user, and in response to the combination of the first amount of light and the second amount of light being out of the reference range, turn On the first switch and turn Off the second switch, and measure the first amount of light into which the light is reflected by the user's body tissue through the first light-receiving unit, or turn Off the first switch and turn On the second switch, and measure the second amount of light into which the light is reflected by the user's body tissue through the second light-receiving unit.

The processor may be configured to, in response to the measured capacitance being out of the range, measure an amount of light received from the first light-receiving unit and the second light-receiving unit, and acquire a biometric signal.

The processor may be configured to, in response to at least one amount of light being an amount of light within a specified range, determine that the electronic device is worn by the user and in response to the first amount of light and the second light being an amount of light out of the specified range, determine that the electronic device is detached from the user.

The processor may be configured to, in response to the first amount of light and the second light being the amount of light out of the specified range, sense a biometric signal for the user based on an amount of light received from the first light-receiving unit or the second light-receiving unit, and determine whether the electronic device is worn by or detached from the user at least based on the biometric signal.

The processor may be configured to, in response to the biometric signal being sensed, determine that the electronic device is worn by the user and in response to the biometric signal not being sensed, determine that the electronic device is detached from the user.

The processor may be configured to, in response to it being determined that the electronic is worn by the user, maintain user authentication of the electronic device, and in response to it being determined that the electronic device is detached from the user, release the user authentication of the electronic device.

The electronic device 101 of various embodiments may include the capacitive sensor 210; the heart rate sensor 200 including the at least one light-emitting unit 220 and the at least one light-receiving unit (e.g., the first light-receiving unit 230 to the fourth light-receiving unit 240); and the processor 120. The processor may be configured to measure capacitance for a user wearing the electronic device, by using the capacitive sensor, emit light by using the light-emitting unit according to the capacitance, measure an amount of light into which the light is reflected by the user's body tissue through the at least one light-receiving unit, and in response to the amount of light corresponding to a first specified condition, determine that the electronic device is worn by the user, and in response to the amount of light corresponding to a second specified condition, emit light by using the light-emitting unit, sense light into which the emitted light is reflected according to a blood flow rate of the user's blood vessel through the at least one light-receiving unit, sense a biometric signal for the user by using the reflected light, and determine that the electronic device is worn by the user, at least based on the biometric signal.

The processor may be configured to output another light of a brightness lower than the specified brightness by using the light-emitting unit, as at least a part of an operation of measuring the amount of light.

The processor may be configured to, in response to the amount of light satisfying the second specified condition, adjust an intensity of light of the light-emitting unit, and sense a biometric signal for the user by using light emitted according to the adjusted intensity of light, and determine that the electronic device is worn by the user, at least based on the biometric signal.

The processor may be configured to obtain biometric signal feature points of predetermined sections associated with the capacitance based on a time point at which the capacitance is obtained within the first range.

The feature point may include at least one of a phase of the biometric signal, an amplitude or a heartbeat.

The processor may be configured to obtain a feature point of a first biometric signal before N seconds at the time point at which the capacitance is obtained within the first range, and obtain a feature point of a second biometric signal after N seconds.

The processor may be configured to compare the obtained feature points, and control user authentication at least based on the comparison result.

The processor may be configured to, in response to the feature point of the biometric signal being the same, maintain user authentication of the electronic device, and in response to the feature point of the biometric signal being different, release the user authentication of the electronic device.

The electronic device 101 of various embodiments may include the capacitive sensor 210; the heart rate sensor 200 including the at least one light-emitting unit 220 and at least one light-receiving unit (e.g., the first light-receiving unit 230 to the fourth light-receiving unit 240); and the processor 120. The processor is configured to measure capacitance for a user wearing the electronic device, by using the capacitive sensor, measure an amount of light through the at least one light-receiving unit according to the capacitance, and in response to the amount of light corresponding to a first specified condition, determine that the electronic device is worn by the user, and in response to the amount of light corresponding to a second specified condition, emit light of a specified brightness by using the light-emitting unit, sense light into which the emitted light is reflected by the user through the at least one light-emitting unit, sense a biometric signal for the user by using the reflected light, and determine that the electronic device is worn by the user, at least based on the biometric signal.

Figure 5:
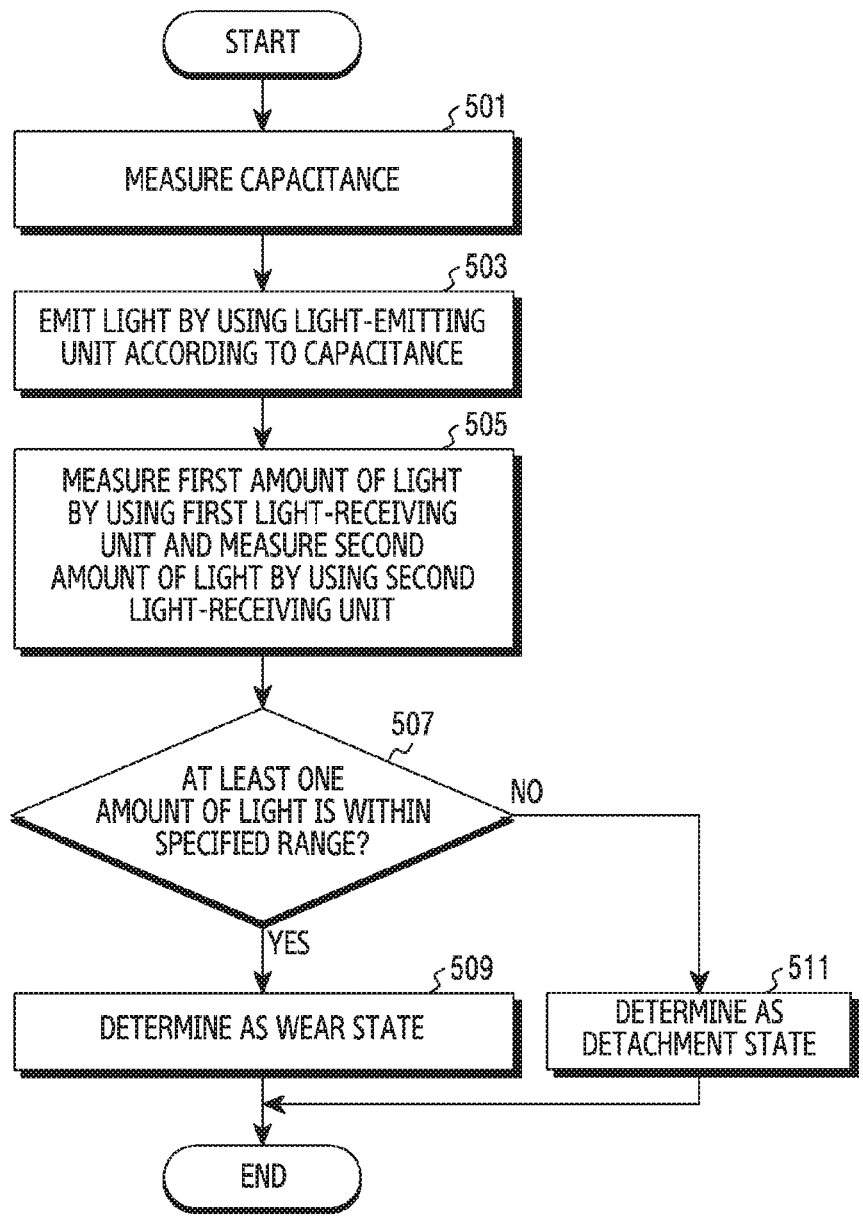
FIG. 5 is a flowchart illustrating an operation method of an electronic device according to various embodiments.

FIG. 5 is a flowchart illustrating an operation method of an electronic device according to various embodiments.

Referring to FIG. 5, in operation 501, the processor 120 of the electronic device 101 may measure capacitance. The processor 120 may acquire raw data measured from the capacitive sensor 210 and calculate capacitance (or capacitance measurement value) for a user who wears the electronic device 101. The processor 120 may perform operation 501 in response to a system of the electronic device 101 being initiated (e.g., power on), in response to the electronic device 101 entering a sleep mode, in response to a display (e.g., the display device 160) of the electronic device 101 turning On and entering an activation state, or throughout system activation.

In operation 503, the processor 120 of the electronic device 101 may emit light by using the light-emitting unit 220 according to the capacitance. The processor 120 of various embodiments may emit light by controlling an intensity of light of the light-emitting unit 220 or an output cycle of light. The processor 120 of various embodiments may emit light irrespective of the capacitance. Or, the processor 120 may emit light in response to the capacitance being within a first range.

In operation 505, the processor 120 of the electronic device 101 may measure a first amount of light by using the first light-receiving unit 230, and measure a second amount of light by using the second light-receiving unit 240. The first light-receiving unit 230 and the second light-receiving unit 240 of various embodiments may receive light into which light emitted by the light-emitting unit 220 is reflected by the user's body tissue. The emitted light may go into and then be reflected and come out from the user's skin surface or the body tissue deeper than the skin surface, or a blood flow (e.g., artery flow) of the blood vessel. The processor 120 of various embodiments may measure a received (or obtained) amount of light, and acquire a direct current (DC) output value. The direct current output value may be measured by using a value which is obtained through the first light-receiving unit 230 or the second light-receiving unit 240 during a time of a few ms or less. Or, the processor 120 may provide a biometric signal, by digitizing and enumerating in sequence an amount of light received (or obtained) through the first light-receiving unit 230 or the second light-receiving unit 240. To provide the biometric signal has to acquire an amount of light during a predetermined time (e.g., 5 seconds, 10 seconds, etc.). In accordance with embodiments, a description is made in which operation 505 acquires only the direct current output value measurable within a few ms.

In operation 507, the processor 120 of the electronic device 101 may determine whether at least one amount of light among amounts of light received through the first light-receiving unit 230 and the second light-receiving unit 240 satisfies a specified condition. For example, the processor 120 may control a switch and measure only a first amount of light wherein it may receive an output value of the first light-receiving unit 230, and determine whether the first amount of light is within a second range. In response to being within the second range, the processor 120 may perform operation 509. In response to the first amount of light being out of the second range, the processor 120 may control the switch and measure only a second amount of light wherein it may receive an output value of the second light-receiving unit 240, and determine whether the second amount of light is within the second range. In response to the second amount of light being within the second range, the processor 120 may perform operation 509. In response to the second amount of light being out of the second range, the processor 120 may perform operation 511.

In response to a reflected amount of light being included in a specified range (e.g., in response to even any one amount of light being within the second range), in operation 509, the processor 120 of the electronic device 101 may determine the electronic device 101 as a wear state. The processor 120 may turn On all the switch, and acquire information on a heartbeat by using an output value of the first light-receiving unit 230 and an output value of the second light-receiving unit 240.

In response the reflected amount of light being out of the specified range (e.g., in response to all of the first amount of light and the second amount of light being out of the second range), in operation 511, the processor 120 of the electronic device 101 may determine the electronic device 101 as a detachment state (e.g., a non-wear state). The processor 120 may control a process related to user authentication.

Figure 6:
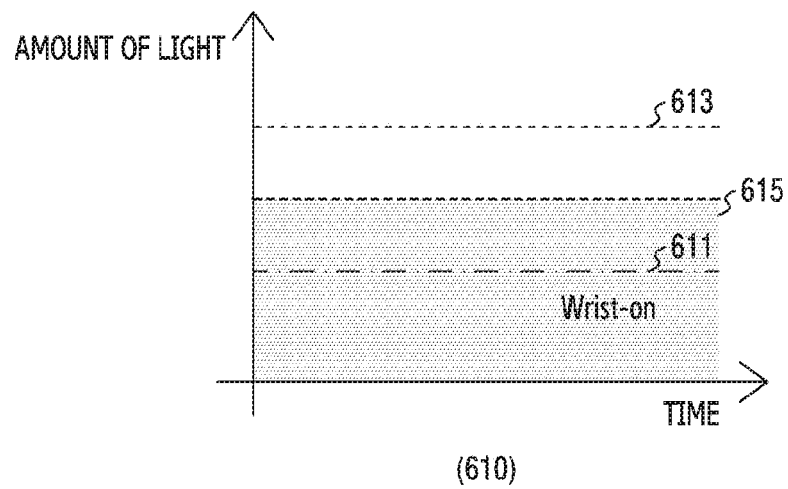
FIG. 6 is a diagram illustrating a graph showing whether an output value of each light-receiving unit exceeds a specified range according to various embodiments.
Figure 6:
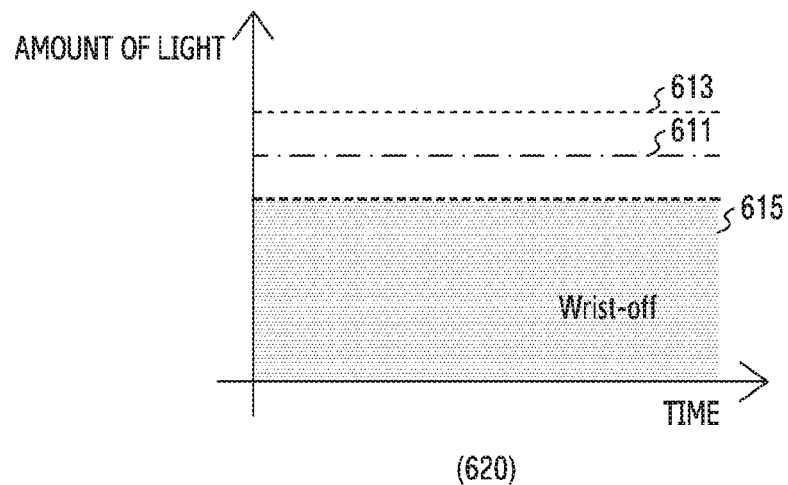

FIG. 6 is a diagram illustrating a graph showing whether an output value of each light-receiving unit exceeds a range according to various embodiments.

Referring to FIG. 6, a first graph 610 illustrates a situation where a first amount of light 611 is within a second range 615, and a second amount of light 613 is out of the second range. The second range 615 is not limited to the illustrated example, and may include a specified section or a specified range. In response to acquiring an output value such as the first graph 610, the processor 120 may determine the electronic device 101 as a wear state. A second graph 620 illustrates a situation where all of the first amount of light 611 and the second amount of light 613 are out of the second range 615. In response to acquiring an output value such as the second graph 620, the processor 120 may determine the electronic device 101 as a detachment state.

Figure 7:
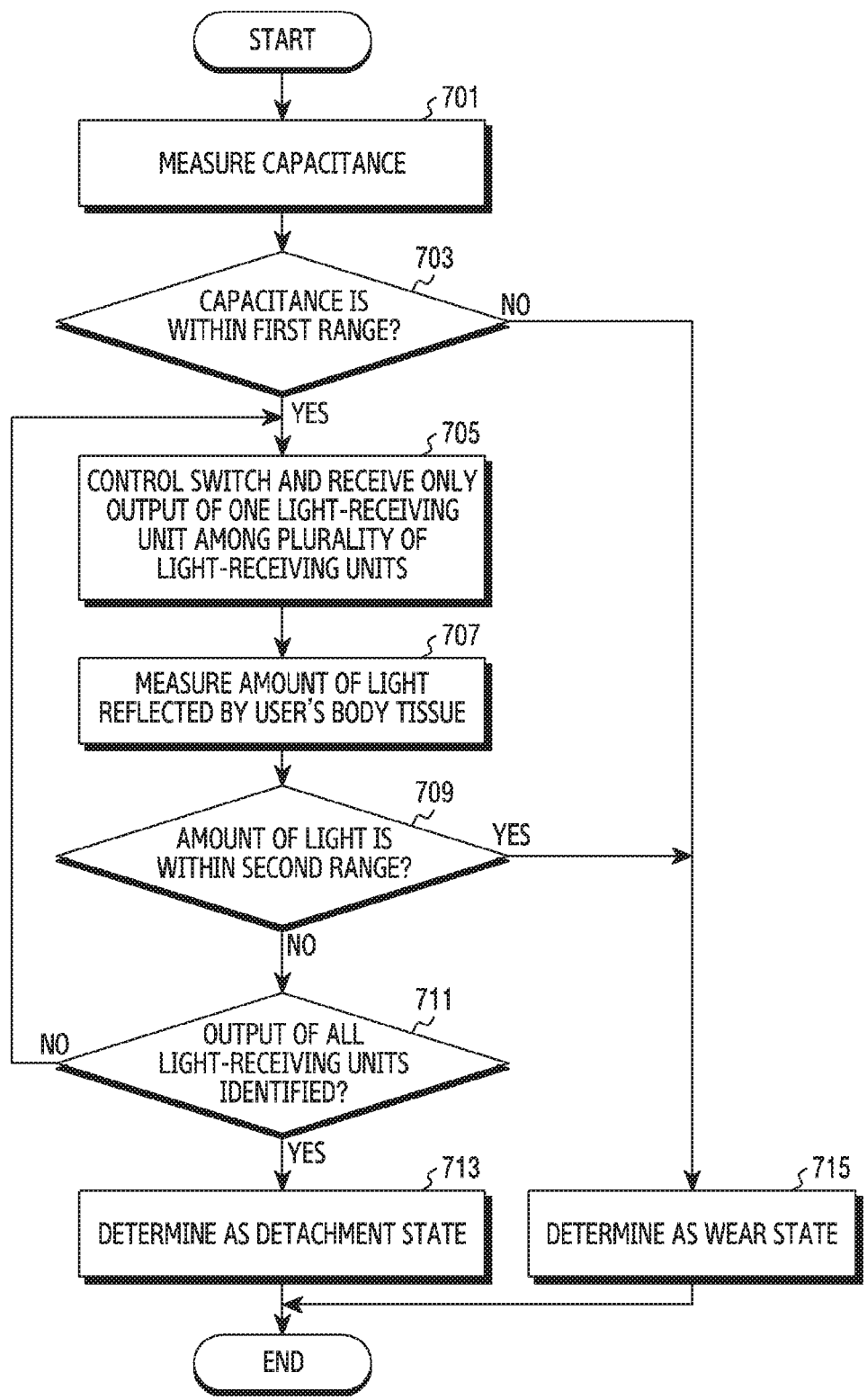
FIG. 7 and FIG. 8 are flowcharts illustrating a method for judging a wear state by using a direct current output value of a light-receiving unit in an electronic device according to various embodiments.
Figure 8:
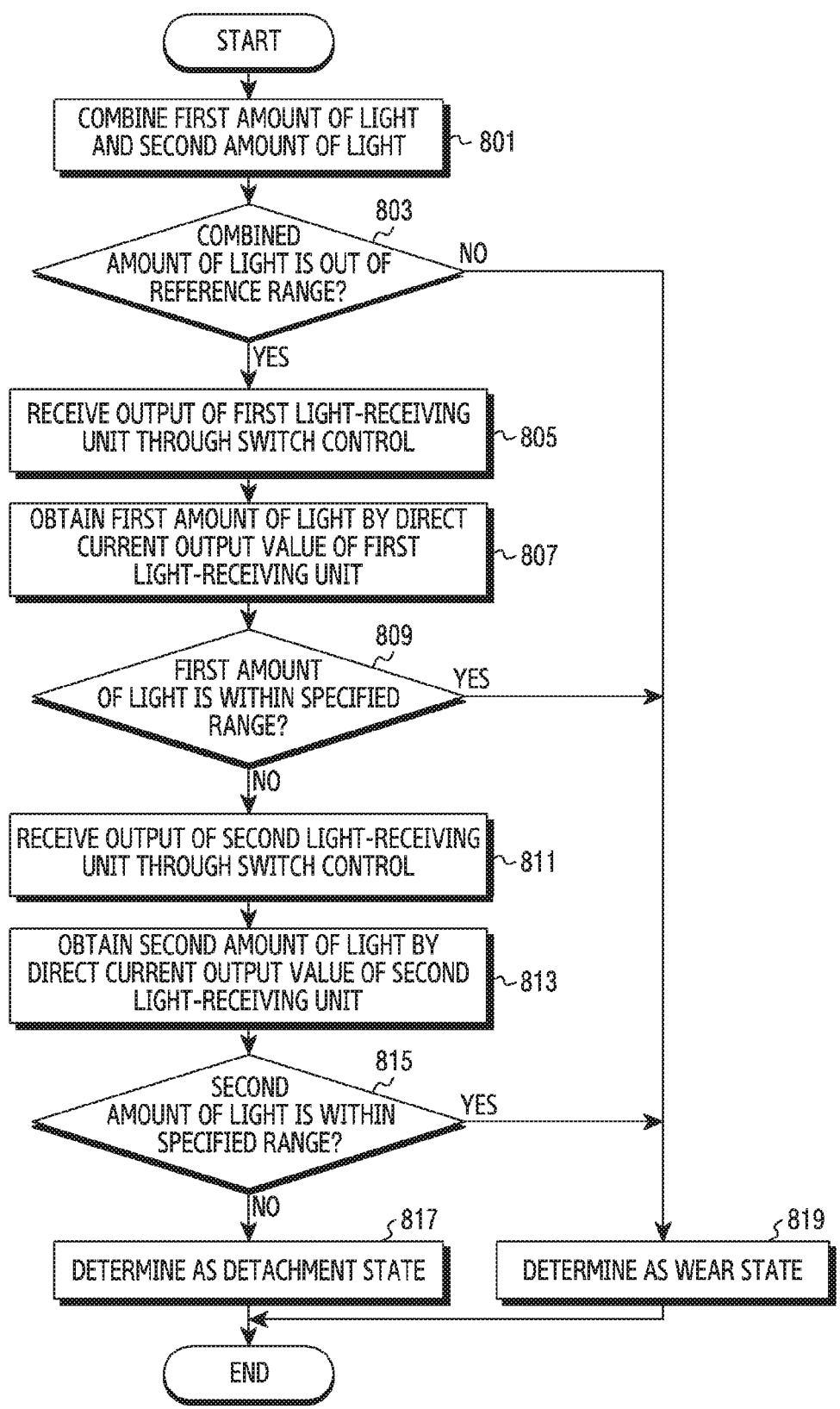

FIG. 7 and FIG. 8 are flowcharts illustrating a method for judging a wear state by using a direct current output value of a light-receiving unit in an electronic device according to various embodiments.

FIG. 7 is a flowchart illustrating a method for judging the wear state by controlling a switch according to capacitance.

Referring to FIG. 7, in operation 701, the processor 120 of the electronic device 101 may measure capacitance. The processor 120 may acquire raw data measured from the capacitive sensor 210 and calculate capacitance (or capacitance measurement value) for a user who wears the electronic device 101.

In operation 703, the processor 120 of the electronic device 101 may determine whether the capacitance is within a first range. A capacitive sensor measurement value (Csensor) in response to a conductive material (e.g., the user's body) not approaching the first electrode 211 and the second electrode 213 of the capacitive sensor 210 may be the same as a capacitance value (Cenv) by a peripheral environment. In response to the conductive material such as the finger or the wrist approaches or gets in contact with the first electrode 211 and the second electrode 213, a measurement value of the capacitive sensor 210 may be increased by a variation of an electric field.

In operation 701 and operation 703, the processor 120 may turn On all the switch 320 (e.g., the first switch 321 and the second switch 322), and receive all the output of the plurality of light-receiving units 230 to 240.

In response to the capacitance being out of the first range, the processor 120 may perform operation 715. In response to the capacitance being within the first range, the processor 120 may perform operation 705.

In operation 705, the processor 120 of the electronic device 101 may control the switch 320 and receive only the output of one light-receiving unit among the plurality of light-receiving units 230 to 240. For example, in response to the electronic device 101 being implemented as a circuit diagram of FIG. 4A, the processor 120 may turn On the first switch 321 and turn Off the second switch 322, and receive only the output of the first light-receiving unit 230. Or, the processor 120 may turn Off the first switch 321 and turn On the second switch 322, and receive only the output of the second light-receiving unit 240.

In operation 707, the processor 120 of the electronic device 101 may measure an amount of light reflected by the user's body tissue. The processor 120 may measure a first amount of light based on a value received from the first light-receiving unit 230. Or, the processor 120 may measure a second amount of light based on a value received from the second light-receiving unit 240. At this time, the processor 120 may measure an amount of light by using a value (e.g., a direct current output value) which is obtained during a time of a few ms through the first light-receiving unit 230 or the second light-receiving unit 240.

In operation 709, the processor 120 of the electronic device 101 may determine whether an amount of light received through the first light-receiving unit 230 or the second light-receiving unit 240 is within a second range. For example, the processor 120 may determine whether the first amount of light received through the first light-receiving unit 230 is within the second range, or the second amount of light received through the second light-receiving unit 240 is within the second range.

In response to the amount of light (e.g., the first amount of light) being within the second range, the processor 120 may perform operation 715 and, in response to the amount of light being out of the second range, the processor 120 may perform operation 711.

In response to the amount of light being out of the second range, in operation 711, the processor 120 of the electronic device 101 may determine whether all the output of the light-receiving units has been identified. For example, in response to only the output of the first light-receiving unit 230 having been identified in operation 709, the processor 120 may return to operation 705 in order to identify the output of the second light-receiving unit 240. In response to returning to operation 705, the processor 120 may determine whether the output of the second light-receiving unit 240 is less than the second range. In response to the output of the second light-receiving unit 240 being within the second range, the processor 120 may perform operation 715, and in response to the output of the second light-receiving unit 240 being out of the second range, the processor 120 may perform operation 711. In response to all of the output of the first light-receiving unit 230 and the second light-receiving unit 240 being identified in operation 709, the processor 120 may perform operation 713.

In operation 713, the processor 120 of the electronic device 101 may determine the electronic device 101 as a detachment state. In response to all of the first amount of light and the second amount of light being out of the second range, the processor 120 may determine the electronic device 101 as the detachment state (e.g., a non-wear state). The processor 120 may control a process related to user authentication.

In operation 715, in response to any one amount of light among the first amount of light and the second amount of light being within the second range, the processor 120 of the electronic device 101 may determine the electronic device 101 as the wear state. The processor 120 of various embodiments may turn On all the switch 320 (e.g., the first switch 321 and the second switch 322), and receive output values from all the first light-receiving unit 230 and the second light-receiving unit 240. The processor 120 of various embodiments may turn On the switch 320 (e.g., the first switch 321 or the second switch 322) corresponding to at least one light-receiving unit whose a received amount of light is within the second range among the first light-receiving unit 230 and the second light-receiving unit 240, and receive an output value from at least one of the first light-receiving unit 230 and the second light-receiving unit 240.

FIG. 8 is a flowchart illustrating a method for judging a wear state by controlling a switch according to output values of a plurality of light-receiving units.

Referring to FIG. 8, in operation 801, the processor 120 of the electronic device 101 may combine a first amount of light received through the first light-receiving unit 230 and a second amount of light received through the first light-receiving unit 240.

Operation 801 may be performed in response to the capacitance being within the first range in operation 703 of FIG. 7. The processor 120 may turn On all the switch 320 (e.g., the first switch 321 and the second switch 322), and receive all the output of the plurality of light-receiving units 230 to 240. The processor 120 may unite the first amount of light outputted from the first light-receiving unit 230 and the second amount of light outputted from the second light-receiving unit 240.

In operation 803, the processor 120 of the electronic device 101 may determine whether the combined amount of light is out of a reference range. The reference range may be wider or narrower than the second range. For example, in a detachment state, light is received through the light-receiving units 230 to 240 even from an external light source (e.g., sunlight and fluorescent lamp light) besides light emitted from the light-emitting unit 220, so much light may be obtained in the light-receiving units 230 to 240. Accordingly, an amount of light is obtained low (or less) in a wear state, and the amount of light may be obtained high (or much) in the detachment state.

In response to the combined amount of light being out of the reference range, the processor 120 may perform operation 805. In response to the combined amount of light being within the reference range, the processor 120 may perform operation 819.

In operation 805, the processor 120 of the electronic device 101 may receive the output of the first light-receiving unit 230 through the control of the switch 320. For example, in response to the electronic device 101 being implemented as the circuit diagram of FIG. 4A, the processor 120 may turn On the first switch 321 and turn Off the second switch 322, and receive only the output of the first light-receiving unit 230. For example, in response to the electronic device 101 being implemented as the circuit diagram of FIG. 4B, the processor 120 may turn On the first switch 321 and turn Off the second switch 322 to the fourth switch 324, and receive only the output of the first light-receiving unit 230. For example, in response to the electronic device 101 being implemented as the circuit diagram of FIG. 4C, the processor 120 may turn Off the first switch 321 and set control signals S2 and S3 by '00', and receive only the output of the first light-receiving unit 230.

In operation 807, the processor 120 of the electronic device 101 may obtain a first amount of light by a direct current output value of the first light-receiving unit 230. The processor 120 may measure an amount of light which is received by the first light-receiving unit 230 after light emitted by the light-emitting unit 220 is reflected from the user's body tissue.

In operation 809, the processor 120 of the electronic device 101 may determine whether the first amount of light is within the second range. For example, in response to the first amount of light being within the second range, the processor 120 may perform operation 819 and, in response to the first amount of light being out of the second range, the processor 120 may perform operation 811.

In operation 811, the processor 120 of the electronic device 101 may receive the output of the second light-receiving unit 240 through the control of the switch 320. For example, in response to the electronic device 101 being implemented as the circuit diagram of FIG. 4A, the processor 120 may turn Off the first switch 321 and turn On the second switch 322, and receive only the output of the second light-receiving unit 240. For example, in response to the electronic device 101 being implemented as the circuit diagram of FIG. 4B, the processor 120 may turn On the second switch 322, and turn Off the first switch 322, the third switch 323 and the fourth switch 324, and receive only the output of the second light-receiving unit 240. For example, in response to the electronic device 101 being implemented as the circuit diagram of FIG. 4C, the processor 120 may turn Off the first switch 321 and set control signals S2 and S3 by '01', and receive only the output of the second light-receiving unit 240.

In operation 813, the processor 120 of the electronic device 101 may obtain a second amount of light by a direct current output value of the second light-receiving unit 240. The processor 120 may measure an amount of light which is received by the second light-receiving unit 240 after light emitted by the light-emitting unit 220 is reflected from the user's body tissue.

In operation 815, the processor 120 of the electronic device 101 may determine whether the second amount of light is within the second range. For example, in response to the second amount of light being within the second range, the processor 120 may perform operation 819 and, in response to the second amount of light being out of the second range, the processor 120 may perform operation 817.

In operation 817, the processor 120 of the electronic device 101 may determine the electronic device 101 as a detachment state.

In operation 819, in response to any one amount of light among the first amount of light received through the first light-receiving unit 230 and the second amount of light received through the second light-receiving unit 240 being within the second range, the processor 120 of the electronic device 101 may determine the electronic device 101 as a wear state.

Figure 9:
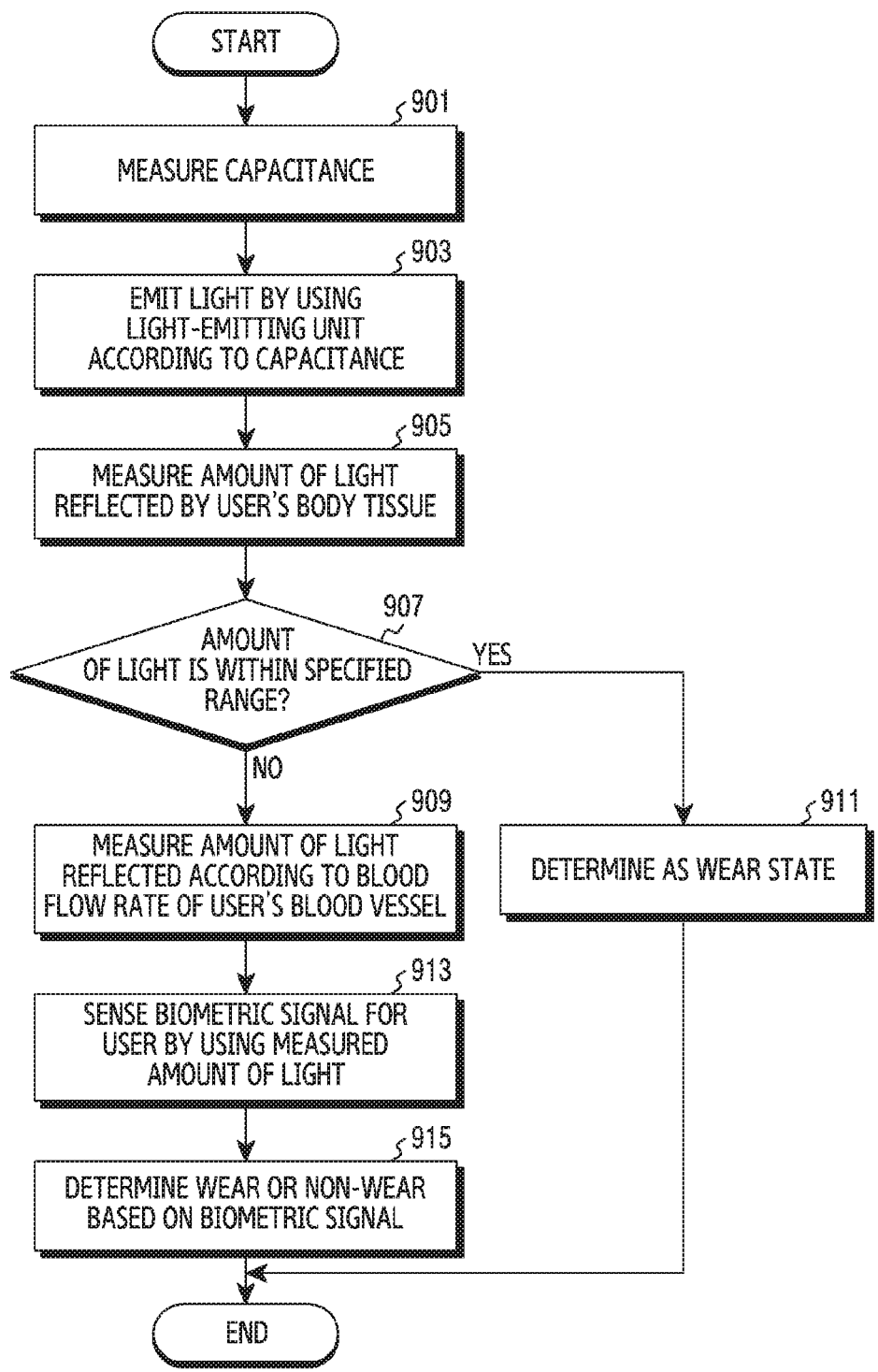
FIG. 9 and FIG. 10 are flowcharts illustrating a method for judging a wear state by using an alternating current output value of a light-receiving unit in an electronic device according to various embodiments.
Figure 10:
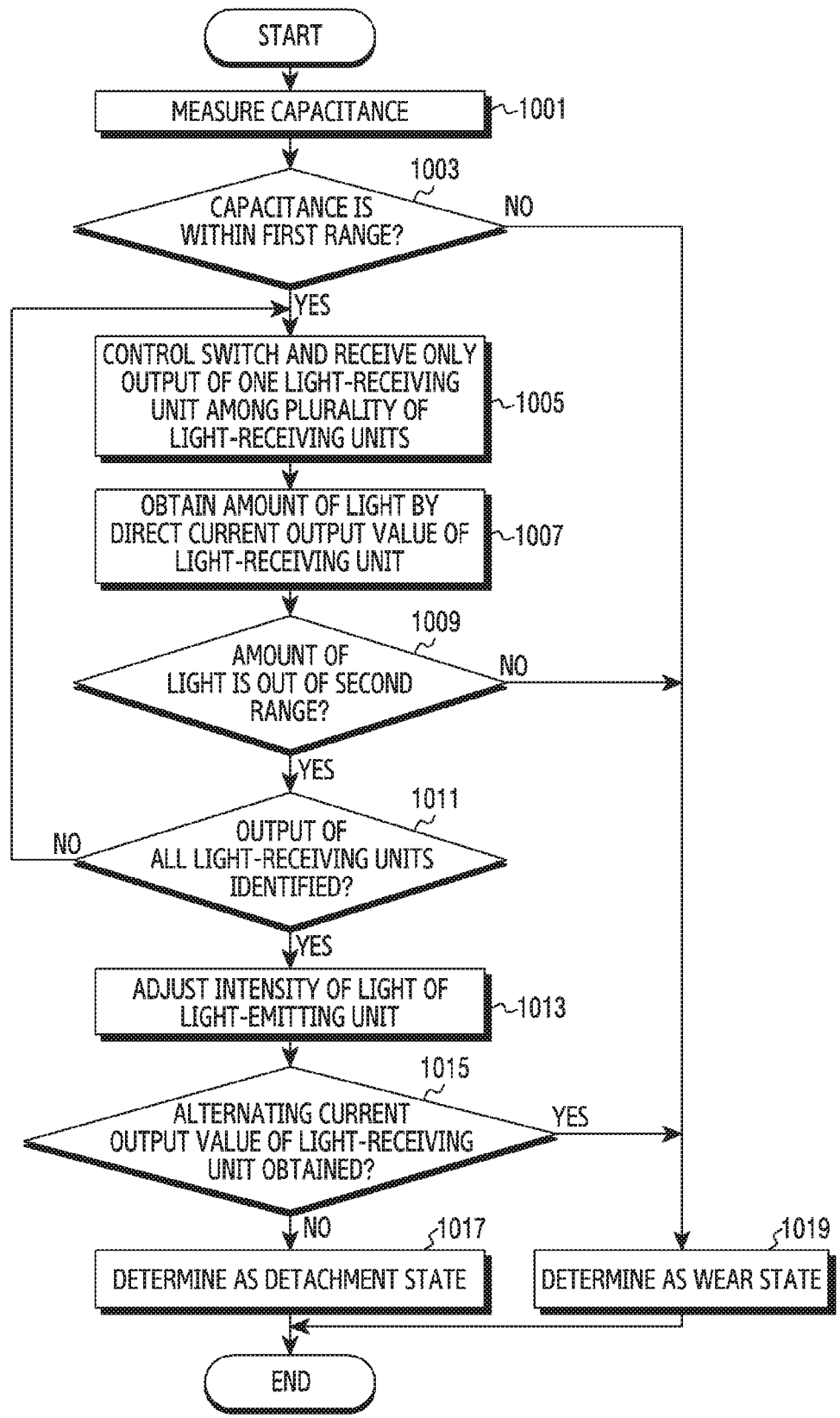

FIG. 9 and FIG. 10 are flowcharts illustrating a method for judging a wear state by using an alternating current output value of a light-receiving unit in an electronic device according to various embodiments.

FIG. 9 is a flowchart illustrating a method for judging the wear state by using the alternating current output value of the light-receiving unit in the electronic device.

Referring to FIG. 9, in operation 901, the processor 120 of the electronic device 101 may measure capacitance.

In operation 903, the processor 120 of the electronic device 101 may emit light by using the light-emitting unit 220 according to the capacitance.

In operation 905, the processor 120 of the electronic device 101 may measure an amount of light which is received by the first light-receiving unit 230 or the second light-receiving unit 240 after light emitted by the light-emitting unit 220 is reflected from the user's body tissue. For example, the processor 120 may measure a first amount of light based on a value outputted from the first light-receiving unit 230. At this time, the processor 120 may measure an amount of light by using a value (e.g., a direct current output value) which is obtained during a time of a few ms through the first light-receiving unit 230.

In operation 907, the processor 120 of the electronic device 101 may determine whether the amount of light received through the first light-receiving unit 230 and the second light-receiving unit 240 corresponds to a condition. For example, the processor 120 may control the switch 320, and measure a first amount of light received from the first light-receiving unit 230, and determine whether the first amount of light is within the second range. In response to being within the second range, the processor 120 may perform operation 911. Or, in response to the first amount of light being out of the second range, the processor 120 may control the switch 320, and measure the second amount of light received from the second light-receiving unit 240, and determine whether the second amount of light is within the second range. In response to the second amount of light being within the second range, the processor 120 may perform operation 911.

In response to the amount of light received through the first light-receiving unit 230 and the second light-receiving unit 240 satisfying a condition (e.g., in response to all of the first amount of light and the second amount of light being out of the second range), in operation 909, the processor 120 of the electronic device 101 may measure an amount of light which is reflected according to a blood flow rate of the user's blood vessel. For example, the processor 120 may measure a variation of an amount of light by using an output value (e.g., an alternating current output value) which is received from at least one light-receiving unit during a predetermined time (e.g., 5 seconds, 10 seconds, etc.). The amount of light measured in operation 905 and the amount of light measured in operation 909 may be different values.

In operation 913, the processor 120 of the electronic device 101 may sense a biometric signal for a user by using the measured amount of light. The biometric signal may be a plethysmogram signal. The biometric signal is calculated using an output value acquired during a predetermined time (e.g., 5 seconds, 10 seconds, etc.) and thus, a time may be required longer than the time measured in operation 905.

In operation 915, the processor 120 of the electronic device 101 may determine wear or non-wear based on the biometric signal. For example, in response to the biometric signal being sensed, the processor 120 may determine the electronic device 101 as a wear state. But, in response to the biometric signal not being sensed, the processor 120 may determine the electronic device 101 as a detachment state (e.g., a non-wear state).

In response to the amount of light received through the first light-receiving unit 230 and the second light-receiving unit 240 satisfying the condition (e.g., in response to even any one amount of light being within the second range), in operation 911, the processor 120 of the electronic device 101 may determine the electronic device 101 as the wear state.

FIG. 10 is a flowchart illustrating a method for judging a wear state by adjusting an intensity of light of a light-emitting unit.

Referring to FIG. 10, in operation 1001, the processor 120 of the electronic device 101 may measure capacitance.

In operation 1003, the processor 120 of the electronic device 101 may determine whether the capacitance is within a first range.

In response to the capacitance being out of the first range, the processor 120 may perform operation 1019. In response to the capacitance being within the first range, the processor 120 may perform operation 1005.

In operation 1005, the processor 120 of the electronic device 101 may control the switch 320, and receive only the output of one light-receiving unit among the plurality of light-receiving units 230 to 240. For example, in response to the electronic device 101 being implemented as the circuit diagram of FIG. 4A, the processor 120 may turn On the first switch 321 and turn Off the second switch 322, and receive only the output of the first light-receiving unit 230. Or, the processor 120 may turn Off the first switch 321 and turn On the second switch 322, and receive only the output of the second light-receiving unit 240.

In operation 1007, the processor 120 of the electronic device 101 may measure an amount of light by a direct current output value of the light-receiving unit. For example, the processor 120 may measure a first amount of light based on a value outputted from the first light-receiving unit 230.

In operation 1009, the processor 120 of the electronic device 101 may determine whether an amount of light is within a second range. For example, the processor 120 may determine whether a first amount of light is within the second range.

In response to the amount of light (e.g., the first amount of light) being within the second range, the processor 120 may perform operation 1019 and, in response to the amount of light being out of the second range, the processor 120 may perform operation 1011.

In response to the amount of light being out of the second range, in operation 1011, the processor 120 of the electronic device 101 may determine whether all the output of the light-receiving units have been identified. For example, in response to only the output of the first light-receiving unit 230 having been identified in operation 1005, the processor 120 may return to operation 1005 in order to identify the output of the second light-receiving unit 240. In response to returning to operation 1005, the processor 120 may control the switch 320 and receive only the output of the second light-receiving unit 240, and determine whether an amount of light outputted from the second light-receiving unit 240 is within the second range. In response to the output of the second light-receiving unit 240 being within the second range, the processor 120 may perform operation 1019 and, in response to the output of the second light-receiving unit 240 being out of the second range, the processor 120 may perform operation 1011. In response to all of the output of the first light-receiving unit 230 and the second light-receiving unit 240 being identified in operation 1011, the processor 120 may perform operation 1013.

In operation 1013, the processor 120 of the electronic device 101 may adjust an intensity of light of the light-emitting unit 220. For example, the processor 120 may control to increase the intensity of light of the light-emitting unit 220 and emit stronger light from the light-emitting unit 220. In response to an intensity of an LED light source of the light-emitting unit 220 being increased, even in an unstable situation, the processor 120 may identify an AC component included in light reflected by the user's body tissue through the optical sensor 200.

In operation 1015, the processor 120 of the electronic device 101 may determine whether an alternating current output value is obtained from the light-receiving unit (e.g., the first light-receiving unit 230 or the second light-receiving unit 240). The processor 120 may acquire a value which is received through the light-receiving unit during a predetermined time for the sake of obtaining of the alternating current output value. The alternating current output value corresponds to a biometric signal. In response to the biometric signal being sensed, the processor 120 may determine the electronic device 101 as a wear state. But, in response to the biometric signal not being sensed, the processor 120 may determine the electronic device 101 as a detachment state (e.g., a non-wear state).

In response to the alternating current output value not being obtained, in operation 1017, the processor 120 of the electronic device 101 may determine the electronic device 101 as the detachment state.

In response to the alternating current output value being obtained, in operation 1019, the processor 120 of the electronic device 101 may determine the electronic device 101 as the wear state. The processor 120 may turn On all the switch 320 (e.g., the first switch 321 and the second switch 322), and receive all output values through the first light-receiving unit 230 and the second light-receiving unit 240.

Figure 11:
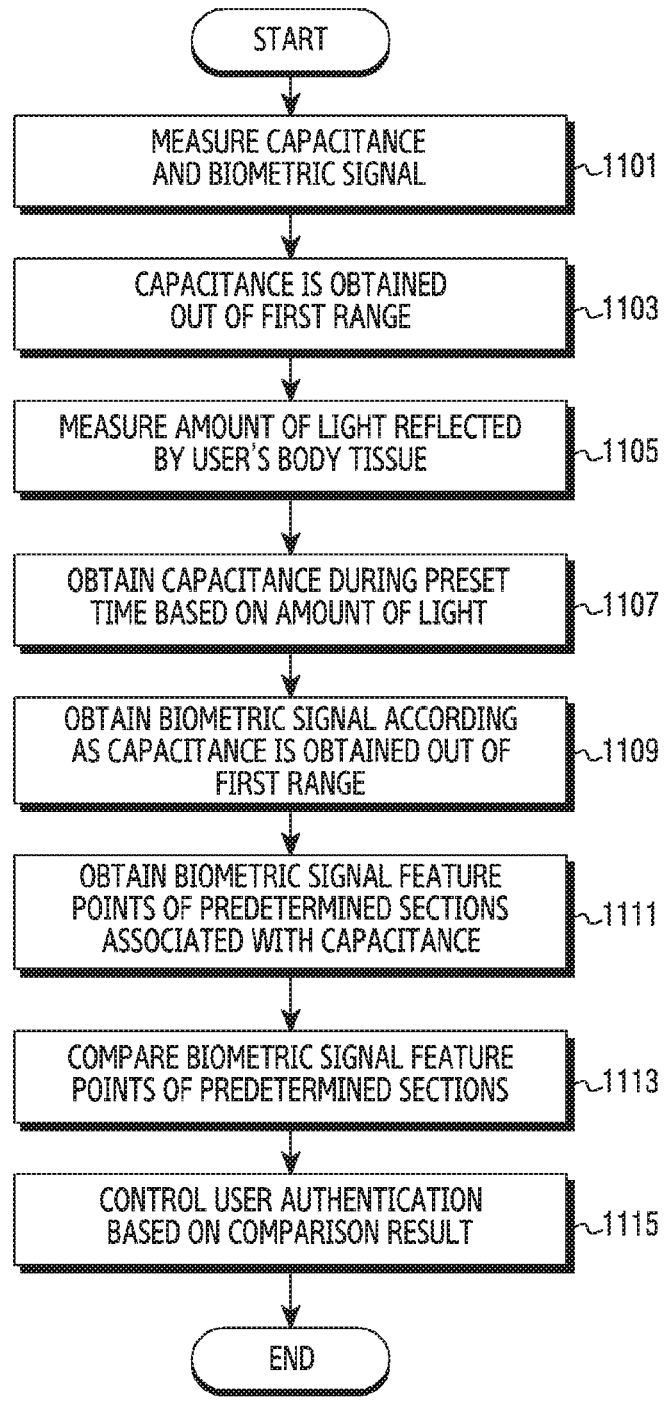
FIG. 11 is a flowchart illustrating a method for controlling user authentication of an electronic device according to various embodiments.

FIG. 11 is a flowchart illustrating a method for controlling user authentication of an electronic device according to various embodiments.

Referring to FIG. 11, in operation 1101, the processor 120 of the electronic device 101 may measure capacitance and a biometric signal. The processor 120 may measure the capacitance by using the capacitive sensor 210, and may measure the biometric signal by using the optical sensor 200.

In operation 1103, the processor 120 of the electronic device 101 may obtain that the capacitance is within a first range. In response to the capacitance being obtained within the first range, the processor 120 may determine that the electronic device 101 is detached.

In operation 1105, the processor 120 of the electronic device 101 may measure an amount of light reflected by the user's body tissue. The processor 120 may measure an amount of light received through one light-receiving unit among the plurality of light-receiving units 230 to 240.

In operation 1107, the processor 120 of the electronic device 101 may obtain capacitance during a preset time based on the amount of light. In various embodiments, in response to the measured amount of light being out of a specified range (or a threshold value), the processor 120 may obtain the capacitance during the preset time. The preset time may include a predetermined time since the capacitance is obtained out of the specified range.

In operation 1109, the processor 120 of the electronic device 101 may obtain the biometric signal according as the capacitance is obtained out of the first range. In various embodiments, in response to the capacitance being obtained out of the first range, the processor 120 may obtain an alternating current output value from a light-receiving unit (e.g., the first light-receiving unit 230 or the second light-receiving unit 240). The obtained alternating current output value may correspond to the biometric signal. In response to the capacitance being obtained out of the first range during the preset time, the processor 120 may determine that the electronic device 101 is detached only during a short time.

In operation 1111, the processor 120 of the electronic device 101 may obtain biometric signal feature points of predetermined sections associated with the capacitance. For example, the processor 120 may obtain a feature point of a first biometric signal of N seconds before a time point at which the capacitance is obtained within the first range. Also, the processor 120 may obtain a feature point of a second biometric signal of N seconds after a time point at which the capacitance is obtained out of the first range. The feature point may include at least one of a phase of the biometric signal, an amplitude or a heart rate.

In operation 1113, the processor 120 of the electronic device 101 may compare the obtained feature point of the first biometric signal and the feature point of the second biometric signal. For example, the processor 120 may determine whether at least one of phases, amplitudes, or heart rates of the feature point of the first biometric signal and the feature point of the second biometric signal is matched.

In operation 1115, the processor 120 of the electronic device 101 may control user authentication based on the comparison result of the feature point of the first biometric signal and the feature point of the second biometric signal. For example, in response to the feature point of the first biometric signal and the feature point of the second biometric signal being similar or identical, the processor 120 may maintain the user authentication. For example, in response to the feature points being, though not completely identical, similar within a predetermined range in consideration of an error value (e.g., corresponding to a similarity degree set to the electronic device 101), the processor 120 may determine that it is the same user. Or, in response to the feature point of the first biometric signal and the feature point of the second biometric signal being mutually different, the processor 120 may release the user authentication. The processor 120 may determine that it is not the same user, and release the user authentication for the sake of security.

For example, in response to the capacitance being obtained within the first range and, within a predetermined time, the capacitance being obtained out of the first range, the processor 120 may identify whether the same user keeps wearing the electronic device 101. In response to the capacitance being obtained out of the first range, it means that the capacitive sensor 210 touches the user's skin tissue and therefore, the processor 120 may measure a heartbeat through the optical sensor 200 (e.g., PPG sensor). In response to the heartbeat patterns of a start time point and end time point of a section in which the capacitance is obtained within the first range being restored and the heartbeat patterns being naturally coupled, the processor 120 may keep judging as a wear state and maintain the user authentication.

Figure 12:
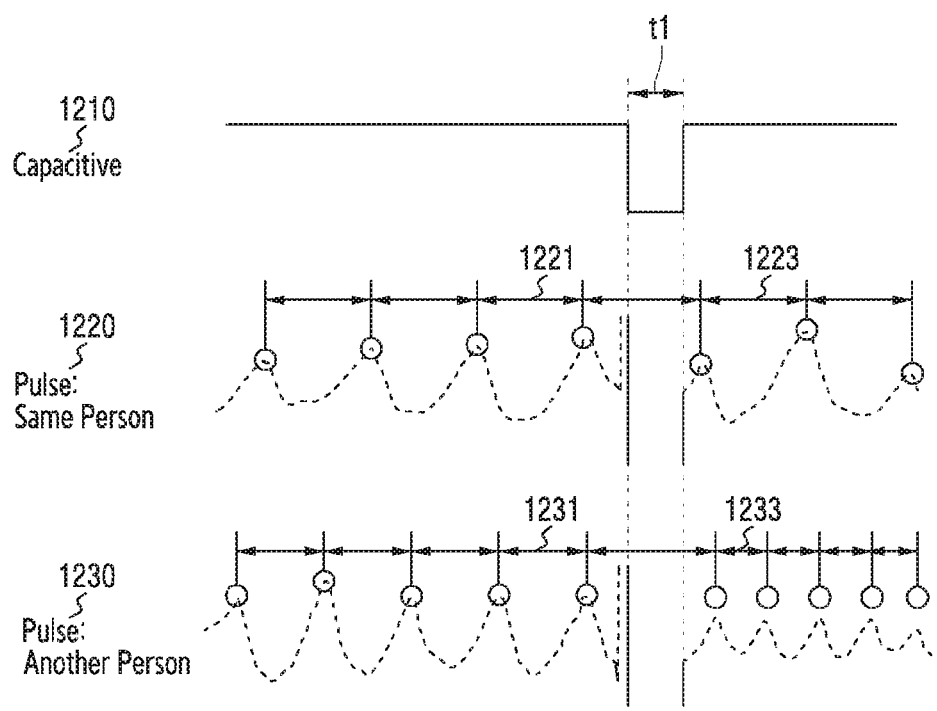
FIG. 12 is a diagram illustrating an example of comparing biometric signals in an electronic device according to various embodiments.

FIG. 12 is a diagram illustrating an example of comparing biometric signals in an electronic device according to various embodiments.

Referring to FIG. 12, the processor 120 may obtain that capacitance 1210 is within a first range at a t1 time point. In this case, the processor 120 may measure biometric signals of predetermined sections (e.g., 1221, 1231) before the t1 and predetermined sections (e.g., 1223, 1233) after the t1. In response to being the same user (1220), a feature point of the first biometric signal 1221 and a feature point of the second biometric signal 1223 may be the same or similar. In response to being determined as the same user, the processor 120 may maintain user authentication. But, in response to users before and after the t1 being different (1230), a feature point of the first biometric 1231 and a feature point of the second biometric signal 1233 may be different. The processor 120 may determine that it is not the same user, and release the user authentication for the sake of security.

Figure 13:
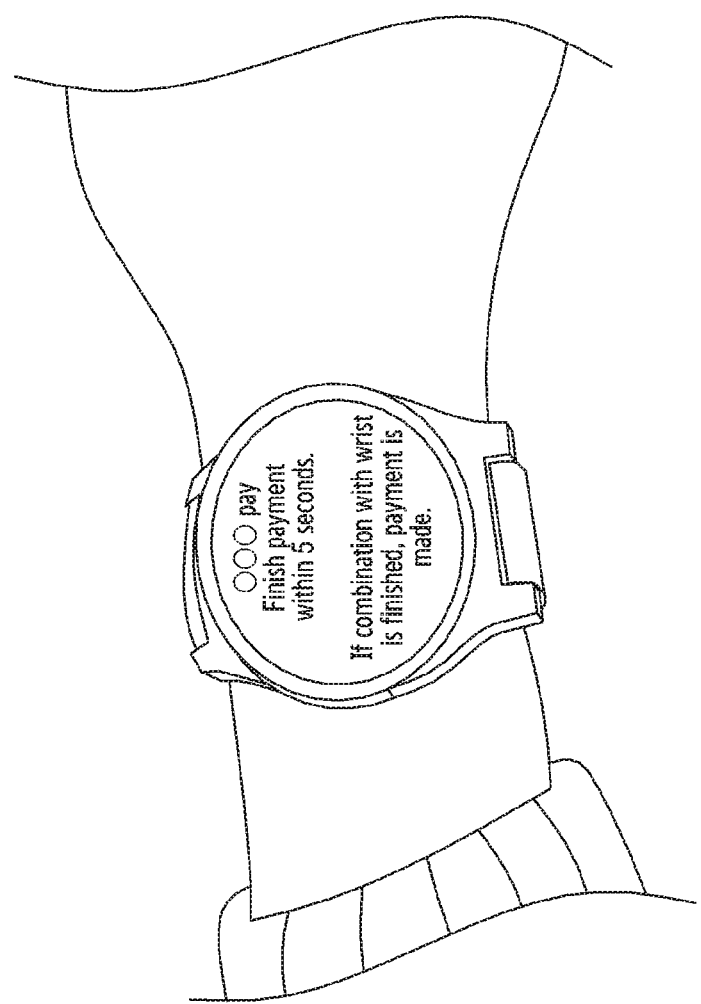
FIG. 13 and FIG. 14 are diagrams illustrating a situation related to user authentication in an electronic device according to various embodiments.
Figure 14:
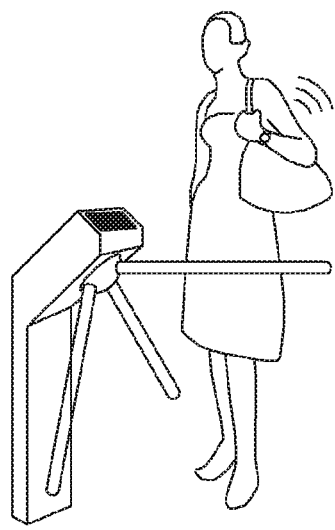
Figure 14:
Figure 14:
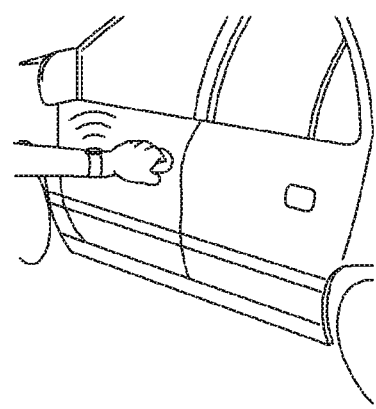
Figure 14:
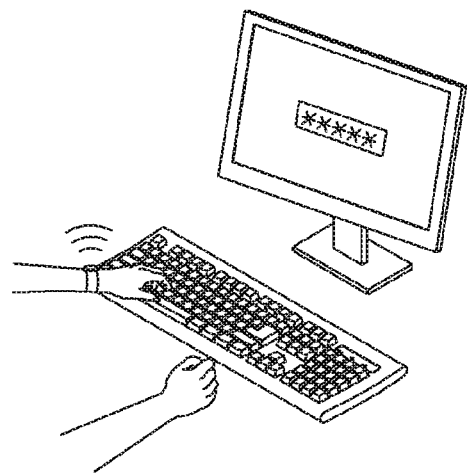

FIG. 13 and FIG. 14 are diagrams illustrating a situation related to user authentication in an electronic device according to various embodiments.

FIG. 13 illustrates a user interface performing user authentication in association with a payment application.

Referring to FIG. 13, in response to a user instantaneously detaching and again wearing the authenticated electronic device 101 within a predetermined time and then requesting for payment, the processor 120 may determine whether the same user keeps wearing. In response to being determined as the same user by comparing the biometric signals as in FIG. 12, the processor 120 may grant payment and in response to not being determined as the same user, the processor 120 may refuse the payment.

FIG. 14 is a diagram illustrating an example of presenting a user authentication service by using the electronic device 101.

Referring to FIG. 14, for example, a first situation 1410 is to perform user authentication by using the electronic device 101 in response to entering into a security zone (e.g., building inside, a predetermined space). In response to the electronic device 101 being detached and then being again worn within a predetermined time and then being requested for security zone entrance, the processor 120 may determine whether the same user keeps wearing. In response to the same user being determined by comparing biometric signals before detachment is sensed and after wear is sensed, the processor 120 may grant the entrance and in response to the same user not being determined, the processor 120 may refuse the entrance. In response to the entrance being granted, the processor 120 may transmit (e.g., Bluetooth, NFC, etc.) information (e.g., an entrance number, a grant number, a user number, etc.) necessary for entrance into the security zone, stored in the memory 130.

For example, a second situation 1420 is to perform user authentication by using the electronic device 101 at online payment. In response to the electronic device 101 being detached and then being again worn within a predetermined time and then being requested for online payment, the processor 120 may determine whether it is the same user, and grant or refuse the payment. For example, a third situation 1430 is to perform user authentication by using the electronic device 101 at the time of releasing a car door lock (or automatic lock release). In response to the electronic device 101 being detached and then being again worn within a predetermined time and then being requested for car door lock release, the processor 120 may determine whether it is the same user, and grant or refuse the door lock release. For example, a fourth situation 1440 is to perform user authentication by using the electronic device 101 at user account log-in. In response to detachment being made and wear being again made within a predetermined time and then the user account log-in being requested, the processor 120 may determine whether it is the same user, and perform the log-in, or not perform.

The electronic device according to various embodiments may be one of various types of electronic devices. The electronic devices may include, for example, a portable communication device (e.g., a smart phone), a computer device, a portable multimedia device, a portable medical device, a camera, a wearable device, or a home appliance. According to an embodiment of the disclosure, the electronic devices are not limited to those described above.

It is to be understood that a singular form corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to." "connected with." or "connected to" another element (e.g., a second element), it means that the element may be coupled with the other element directly (e.g., wired), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PLAYSTORE), or between two user devices (e.g., smart phones) directly. If distributed online, at least part of the computer program product may be temporarily generated or at least temporarily stored in the machine-readable storage medium, such as memory of the manufacturers server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

The invention claimed is:

1. An electronic device comprising:
    a capacitive sensor;
    a heart rate sensor disposed in one surface of the electronic device and comprising at least one light-emitting unit disposed in a first region of the one surface, a first light-receiving unit disposed in a second region of the one surface, and a second light-receiving unit disposed in a third region of the one surface; and
    a processor,
    wherein the processor is configured to:
    measure capacitance for a user wearing the electronic device by using the capacitive sensor;
    emit light by using the light-emitting unit according to the capacitance;
    measure a first amount of light into which the light is reflected by the user's body tissue through the first light-receiving unit, and a second amount of light into which the light is reflected by the body tissue through the second light-receiving unit;
    determine that the electronic device is worn by the user in response to at least one amount of light among the first amount of light measured in the first light-receiving unit and the second amount of light measured in the second light-receiving unit satisfying a specified amount of light;
    determine that the electronic device is detached from the user in response to the first amount of light measured in the first light-receiving unit and the second amount of light measured in the second light-receiving unit not satisfying the specified amount of light; and
    in response to the first amount of light and the second amount of light not satisfying the amount of light of a specified range, further sense a biometric signal for the user based on the amount of light received from the first light-receiving unit or the second light-receiving unit, and determine whether the electronic device is worn by or detached from the user at least based on the biometric signal.

2. The electronic device of claim 1, wherein the processor is configured to measure any one amount of light received from the first light-receiving unit or the second light-receiving unit in response to the measured capacitance being within a specified range.

3. The electronic device of claim 2, wherein the processor is configured to, in response to the measured capacitance being out of the specified range, measure an amount of light received from the first light-receiving unit and the second light-receiving unit, and acquire a biometric signal.

4. The electronic device of claim 1, comprising:
    a first switch for selectively coupling the first light-receiving unit and the processor; and
    a second switch for selectively coupling the second light-receiving unit and the processor,
    wherein the processor is configured to:
    in response to the measured capacitance being within a specified range, turn On the first switch and turn Off the second switch, and measure the first amount of light into which the light is reflected by the user's body tissue through the first light-receiving unit, or turn Off the first switch and turn On the second switch, and measure the second amount of light into which the light is reflected by the user's body tissue through the second light-receiving unit.

5. The electronic device of claim 4, wherein the processor is configured to, in response to the first amount of light satisfying an amount of light of the specified range, determine that the electronic device is worn by the user, and turn On the second switch.

6. The electronic device of claim 4, wherein the processor is configured to:
    in response to the first amount of light not satisfying an amount of light of the specified range, turn Off the first switch and turn On the second switch, and measure the second amount of light into which the light is reflected by the user's body tissue through the second light-receiving unit, and in response to the second amount of light satisfying the amount of light of the specified range, determine that the electronic device is worn by the user, and turn On the first switch.

7. The electronic device of claim 4, wherein the processor is configured to:
    in response to the first switch being turned On and the second switch being turned On and a combination of the first amount of light and the second amount of light being within a reference range, determine that the electronic device is worn by the user, and
    in response to the combination of the first amount of light and the second amount of light being out of the reference range, turn On the first switch and turn Off the second switch, and measure the first amount of light into which the light is reflected by the user's body tissue through the first light-receiving unit, or turn Off the first switch and turn On the second switch, and measure the second amount of light into which the light is reflected by the user's body tissue through the second light-receiving unit.

8. An electronic device comprising:
a capacitive sensor;
a heart rate sensor comprising at least one light-emitting unit and at least one light-receiving unit; and
a processor,
wherein the processor is configured to:
measure capacitance for a user wearing the electronic device, by using the capacitive sensor;
emit light by using the light-emitting unit according to the capacitance;
measure an amount of light into which the light is reflected by the user's body tissue through the at least one light-receiving unit;
in response to the amount of light corresponding to a first specified range, determine that the electronic device is worn by the user;
in response to the amount of light corresponding to a second specified range, emit light by using the light-emitting unit, sense light into which the emitted light is reflected according to a blood flow rate of the user through the at least one light-receiving unit, sense a biometric signal for the user by using the reflected light, and determine that the electronic device is worn by the user, at least based on the biometric signal; and
in response to the amount of light corresponding to the second specified range, adjust an intensity of light of the light-emitting unit, and sense a biometric signal for the user by using light emitted according to the adjusted intensity of light, and determine that the electronic device is worn by the user, at least based on the biometric signal.

9. The electronic device of claim 8, wherein the processor is configured to obtain biometric signal feature points of predetermined sections associated with the capacitance based on a time point at which the capacitance is obtained within the first specified range.

10. The electronic device of claim 9, wherein the feature point comprises at least one of a phase of the biometric signal, an amplitude or a heartbeat.

11. The electronic device of claim 9, wherein the processor is configured to obtain a feature point of a first biometric signal before a specified time at the time point at which the capacitance is obtained within the first specified range, and obtain a feature point of a second biometric signal after the specified time.

12. The electronic device of claim 11, wherein the processor is configured to compare the feature point of the first biometric signal and the feature point of the second biometric signal, and control user authentication at least based on the comparison result.

13. An electronic device comprising:
a capacitive sensor;
a heart rate sensor comprising at least one light-emitting unit and at least one light-receiving unit; and
a processor,
wherein the processor is configured to:
measure capacitance for a user wearing the electronic device, by using the capacitive sensor;
measure an amount of light through the at least one light-receiving unit according to the capacitance;
in response to the amount of light corresponding to a first specified range, determine that the electronic device is worn by the user;
in response to the amount of light corresponding to a second specified range, emit light of a specified brightness by using the light-emitting unit, sense light into which the emitted light is reflected by the user through the at least one light-emitting unit, sense a biometric signal for the user by using the reflected light, and determine that the electronic device is worn by the user, at least based on the biometric signal; and
in response to the amount of light corresponding to the second specified range, adjust an intensity of light of the light-emitting unit, and sense a biometric signal for the user by using light emitted according to the adjusted intensity of light, and determine that the electronic device is worn by the user, at least based on the biometric signal.

* * * * *